United States Patent
Jenney et al.

(10) Patent No.: US 6,999,821 B2
(45) Date of Patent: Feb. 14, 2006

(54) BODY IMPLANTABLE LEAD INCLUDING ONE OR MORE CONDUCTIVE POLYMER ELECTRODES AND METHODS FOR FABRICATING SAME

(75) Inventors: Christopher R. Jenney, Valencia, CA (US); Sheldon Williams, Green Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 559 days.

(21) Appl. No.: 10/052,776

(22) Filed: Jan. 18, 2002

(65) Prior Publication Data

US 2003/0139794 A1 Jul. 24, 2003

(51) Int. Cl.
*A61N 1/05* (2006.01)

(52) U.S. Cl. ........................................ 607/122; 600/374
(58) Field of Classification Search ......... 600/373–382; 607/115–130
See application file for complete search history.

(56) References Cited

U.S. PATENT DOCUMENTS

| | | | | |
|---|---|---|---|---|
| 3,815,611 A | 6/1974 | Denniston, III | ......... | 128/419 D |
| 4,573,480 A | 3/1986 | Hirschberg | ................. | 128/784 |
| 5,029,585 A | * 7/1991 | Lieber et al. | ............... | 600/396 |
| 5,090,422 A | 2/1992 | Dahl et al. | ................... | 128/784 |
| 5,143,089 A | 9/1992 | Alt | ............................. | 128/784 |
| 5,190,052 A | 3/1993 | Schroeppel | ................. | 128/786 |
| 5,211,174 A | 5/1993 | Imran | .......................... | 128/639 |
| 5,330,520 A | 7/1994 | Maddison et al. | .......... | 607/122 |
| 5,330,521 A | 7/1994 | Cohen | ........................ | 607/122 |
| 5,331,959 A | 7/1994 | Imran | .......................... | 128/639 |
| 5,385,577 A | 1/1995 | Maurer et al. | ................ | 607/41 |
| 5,411,527 A | 5/1995 | Alt | .................................. | 607/5 |
| 5,411,544 A | 5/1995 | Mar et al. | .................... | 607/122 |
| 5,431,681 A | 7/1995 | Helland | ......................... | 607/4 |
| 5,433,742 A | 7/1995 | Willis | .......................... | 607/122 |
| 5,476,496 A | 12/1995 | Strandberg et al. | ......... | 607/122 |

(Continued)

Primary Examiner—Scott M. Getzow

(57) ABSTRACT

A body implantable lead comprises a lead body including a conductive polymer electrode disposed along a distal end portion of the lead body for performing one or more of the functions consisting of pacing, sensing, cardioversion and defibrillation. An electrical conductor, preferably in the form of a multistrand cable conductor, couples the conductive polymer electrode with a proximal end of the lead body. The conductive polymer electrode encapsulates the conductor and is in electrical contact therewith along the length, and preferably along substantially the entire length, of the conductive polymer electrode. The lead body may comprise a multilumen polymer housing, the conductor being contained within one of the lumens of the housing. The conductive polymer electrode may be disposed within a window formed in the lead body. Alternatively, the conductive polymer electrode may comprise multiple electrode sections within a corresponding number of windows formed in the lead body and spaced apart along the length thereof. Further, the window and the conductive polymer electrode disposed therein may extend helically about the lead body. Because of its flexibility and because it can have a small diameter, the lead of the invention is particularly advantageous for implantation in the small, tortuous vessels of the coronary sinus region of the heart for left side stimulation and/or sensing.

Methods of fabricating lead bodies incorporating conductive polymer electrodes are also disclosed.

128 Claims, 20 Drawing Sheets

U.S. PATENT DOCUMENTS

| | | |
|---|---|---|
| 5,534,022 A | 7/1996 | Hoffmann et al. .......... 607/122 |
| 5,554,176 A | 9/1996 | Maddison et al. ............. 607/9 |
| 5,554,178 A | 9/1996 | Dahl et al. .................. 607/122 |
| 5,554,179 A | 9/1996 | Stroetmann et al. ........ 607/129 |
| 5,580,699 A | 12/1996 | Layman et al. ............. 430/311 |
| 5,609,622 A | 3/1997 | Soukup et al. .............. 607/122 |
| 5,645,580 A | 7/1997 | Moaddeb et al. .......... 607/122 |
| 5,658,709 A | 8/1997 | Layman et al. ............. 430/311 |
| 5,681,514 A | 10/1997 | Woody ....................... 264/104 |
| 5,755,766 A | 5/1998 | Chastain et al. ............ 607/122 |
| 5,766,527 A | 6/1998 | Schildgen et al. .......... 264/104 |
| 5,861,023 A | 1/1999 | Vachon ....................... 607/121 |
| 5,902,329 A | 5/1999 | Hoffmann et al. .......... 607/121 |
| 6,295,474 B1 | 9/2001 | Munshi ....................... 607/121 |
| 6,501,992 B1 | 12/2002 | Belden et al. .............. 607/122 |
| 6,574,514 B1 | 6/2003 | Partridge et al. ........... 607/126 |
| 6,718,628 B1 | 4/2004 | Munshi ....................... 29/825 |
| 6,801,809 B1 * | 10/2004 | Laske et al. ................ 607/126 |
| 2002/0111664 A1 | 8/2002 | Bartig et al. ................ 607/122 |
| 2004/0102813 A1 | 5/2004 | Kranz et al. .................... 607/6 |
| 2004/0186545 A1 | 9/2004 | Rosero et al. .............. 607/119 |

* cited by examiner

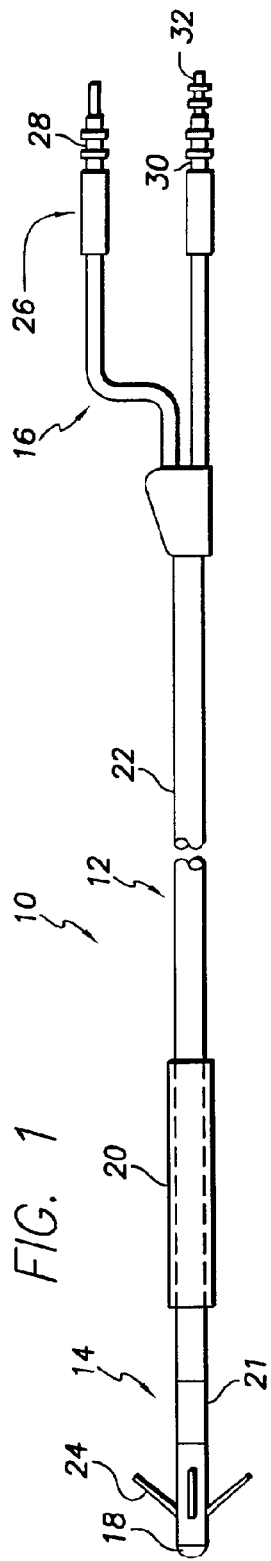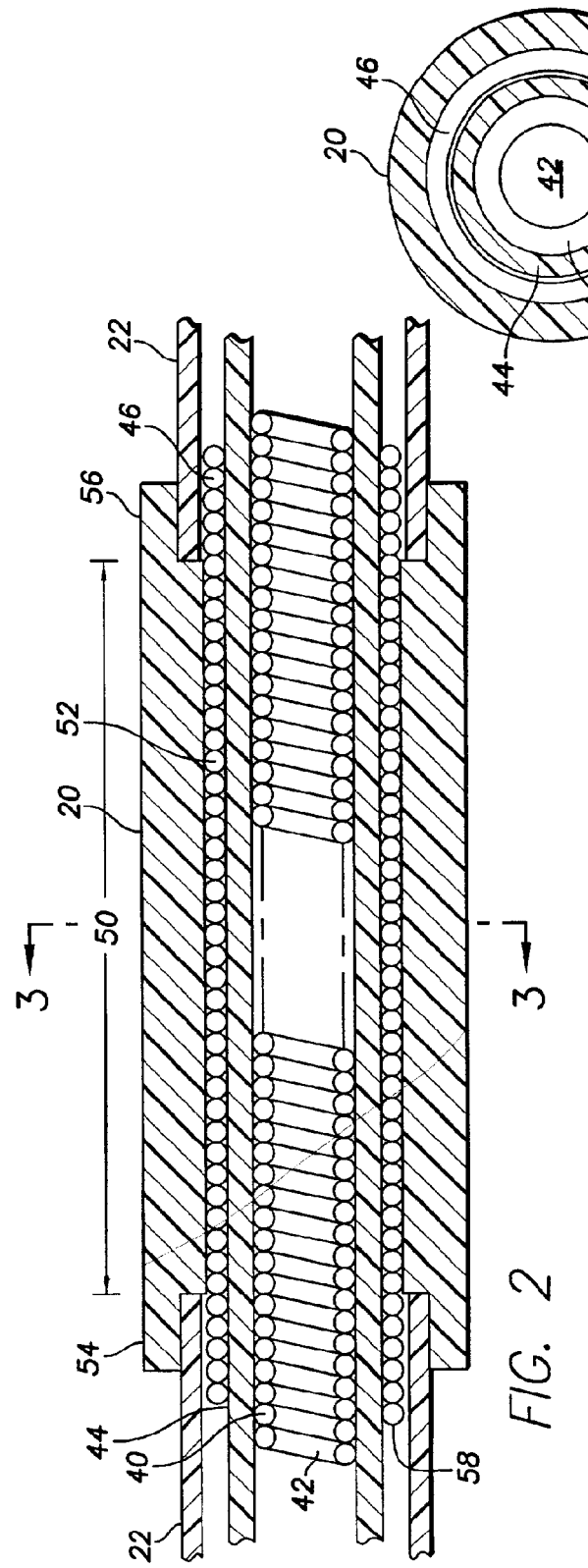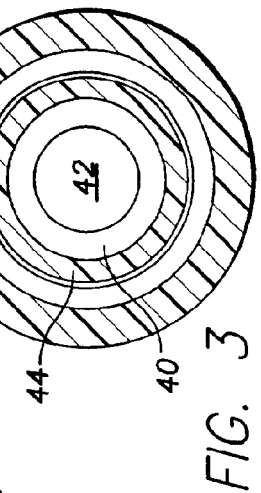

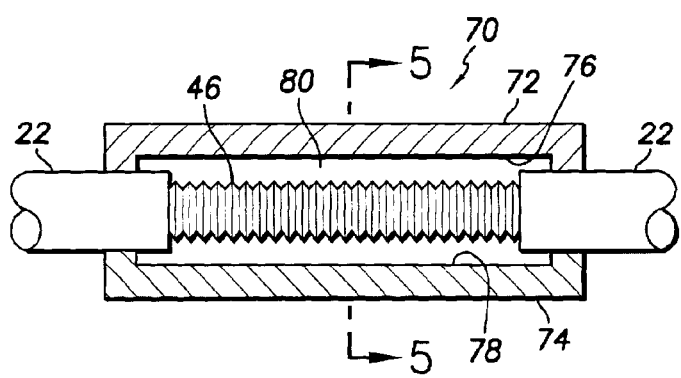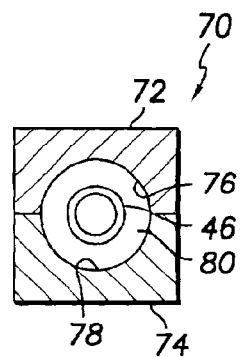
FIG. 4  FIG. 5
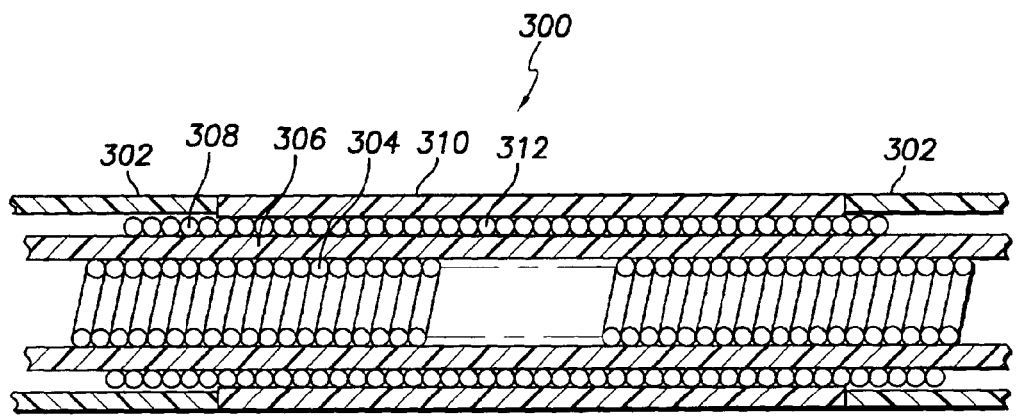
FIG. 6
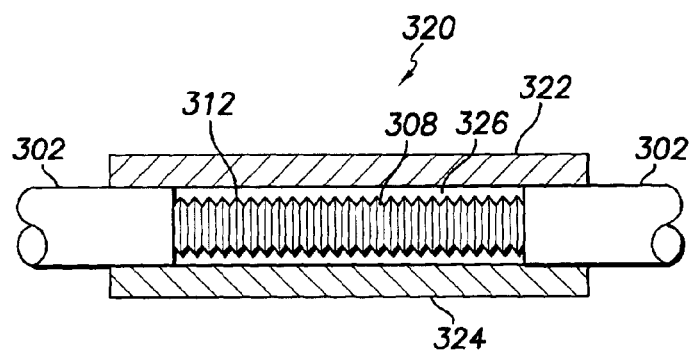
FIG. 7

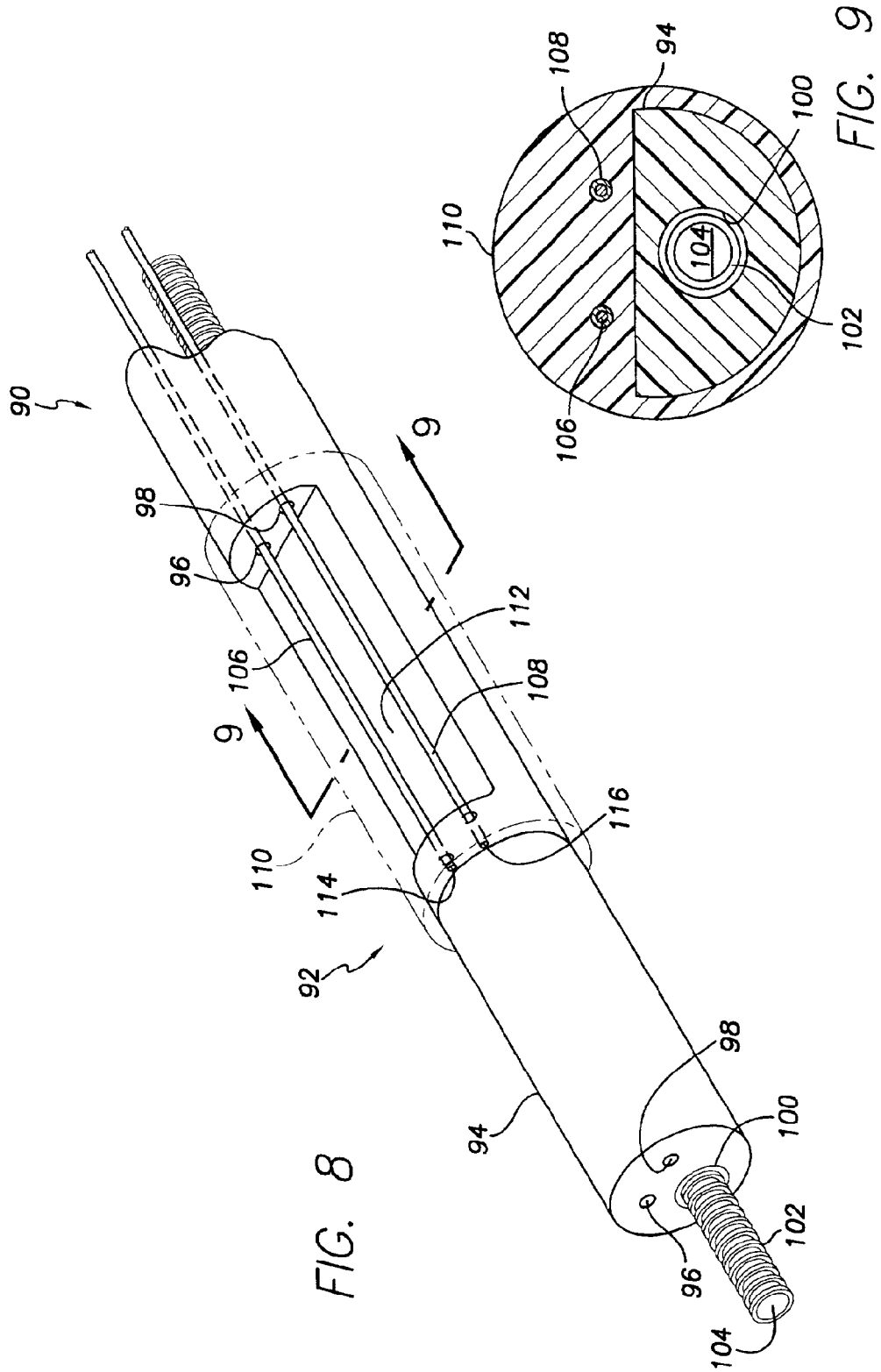

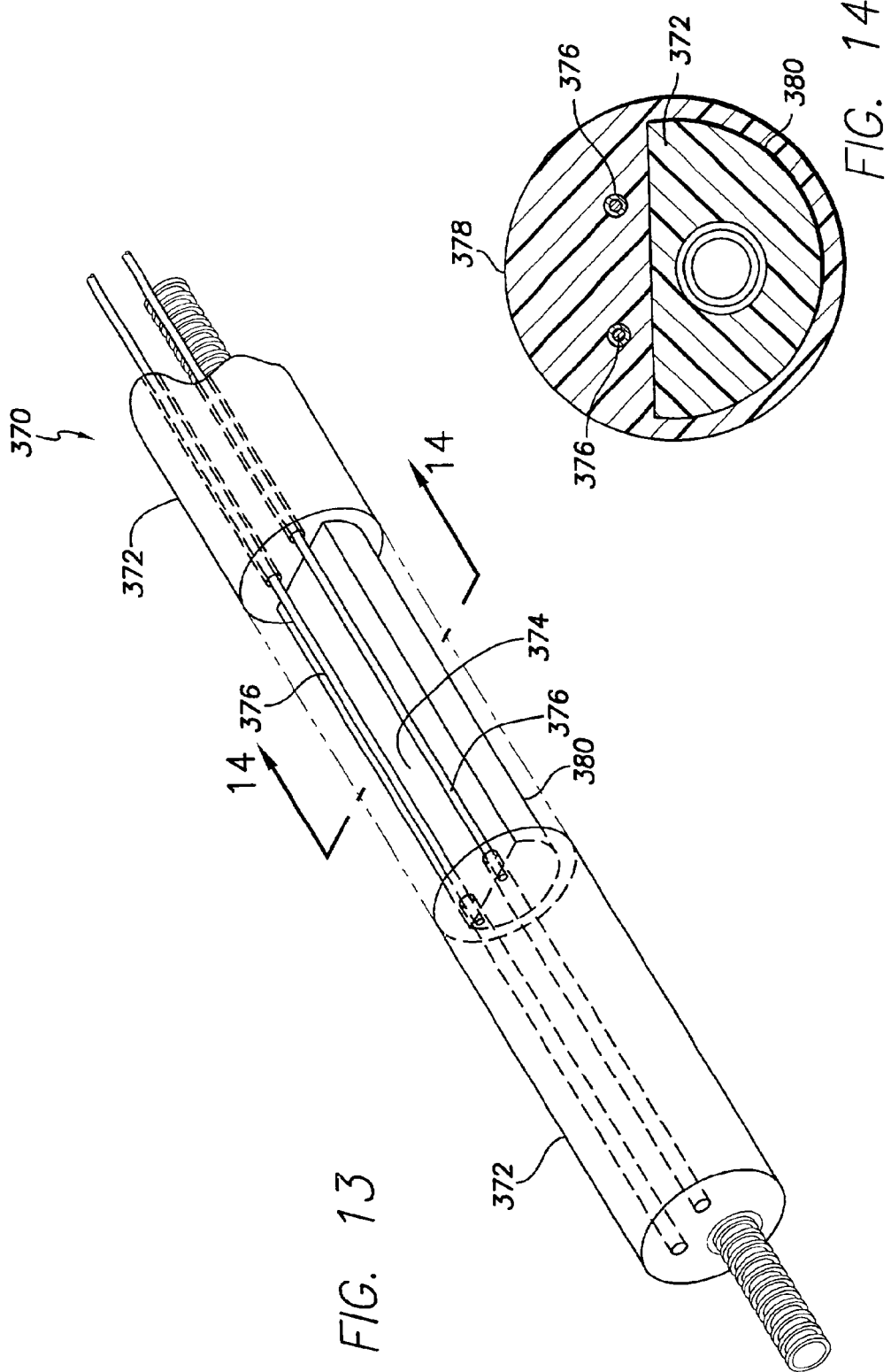

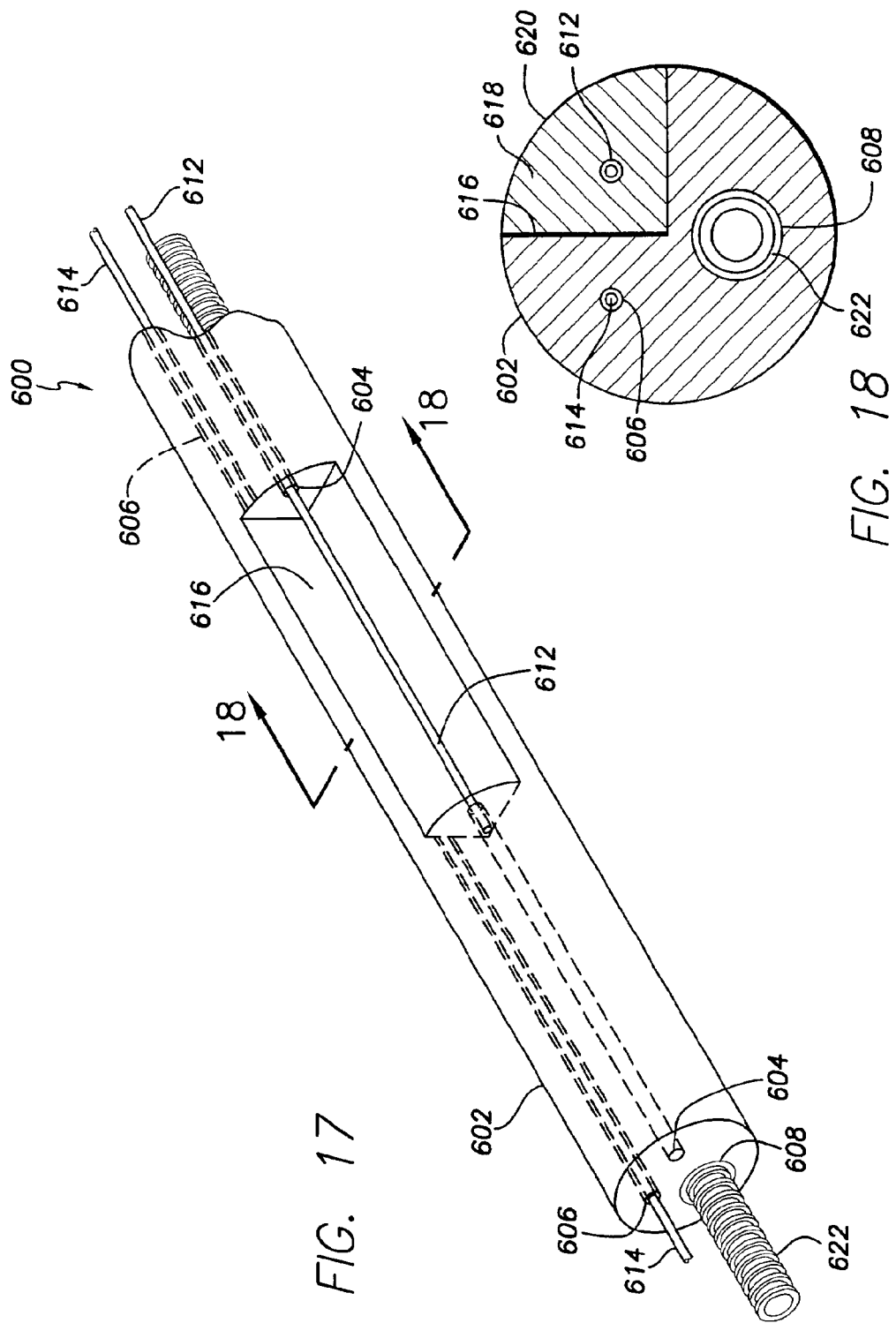

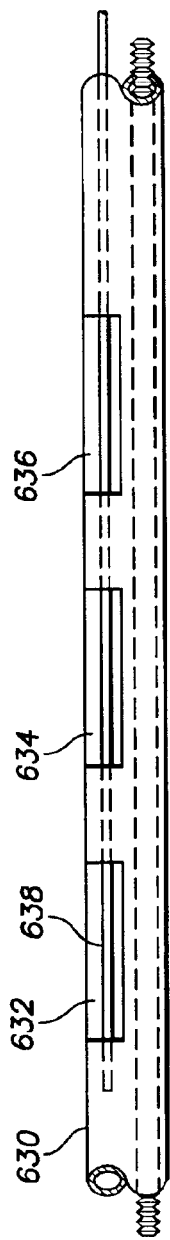
FIG. 19
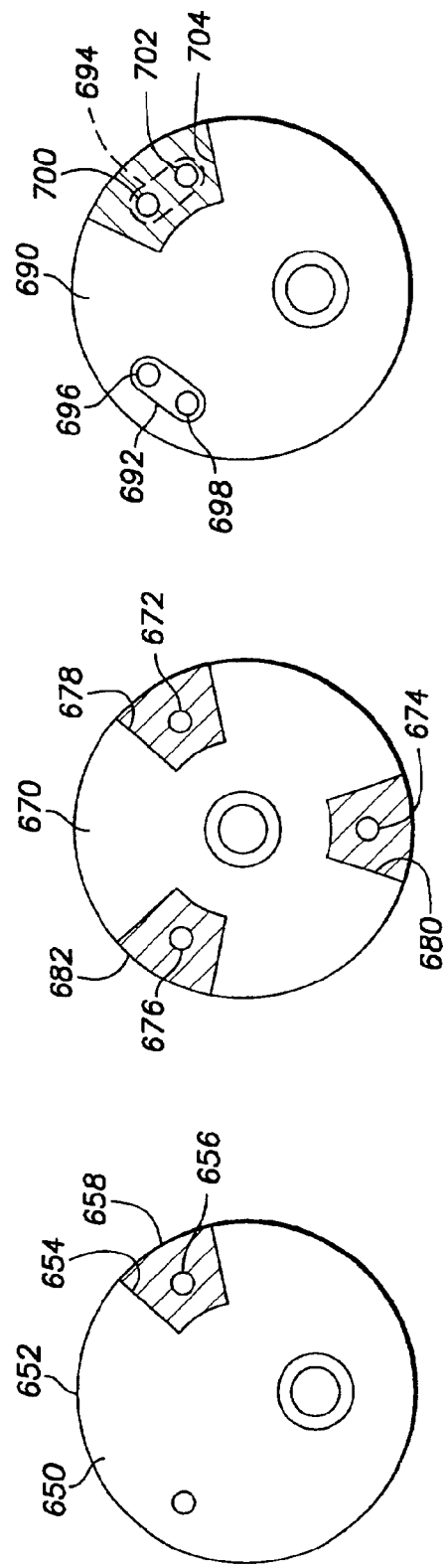
FIG. 22
FIG. 21
FIG. 20

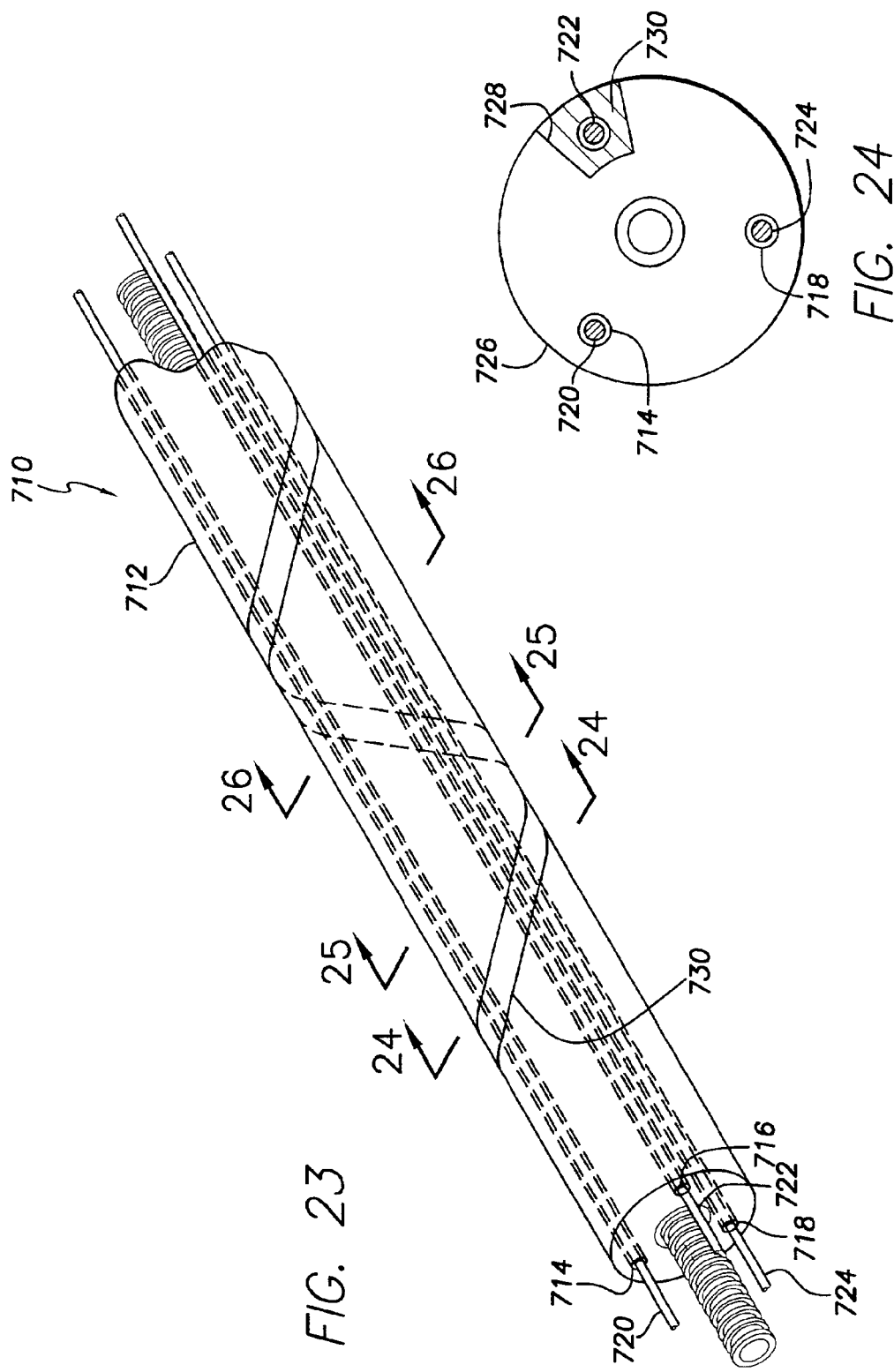

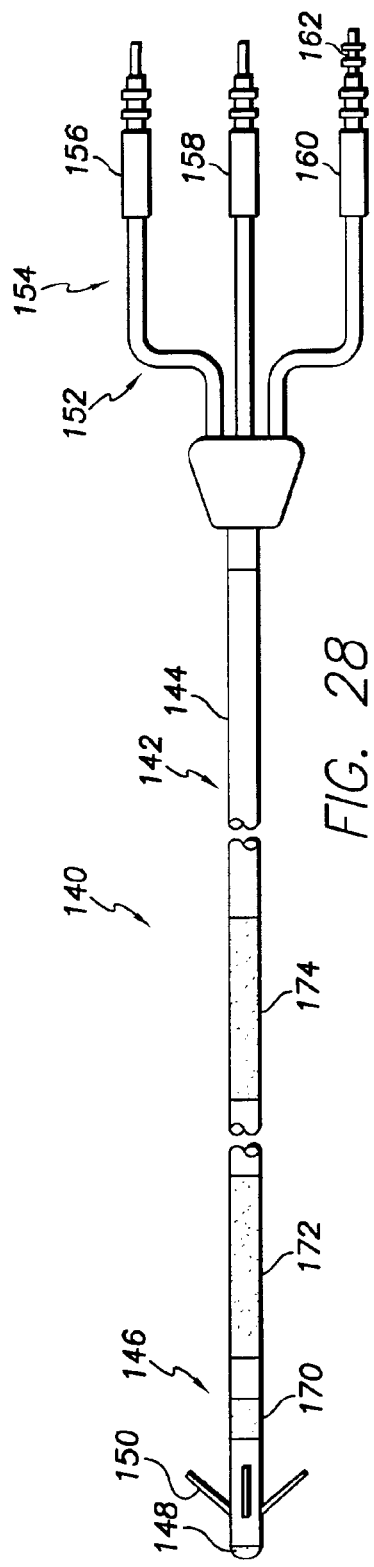
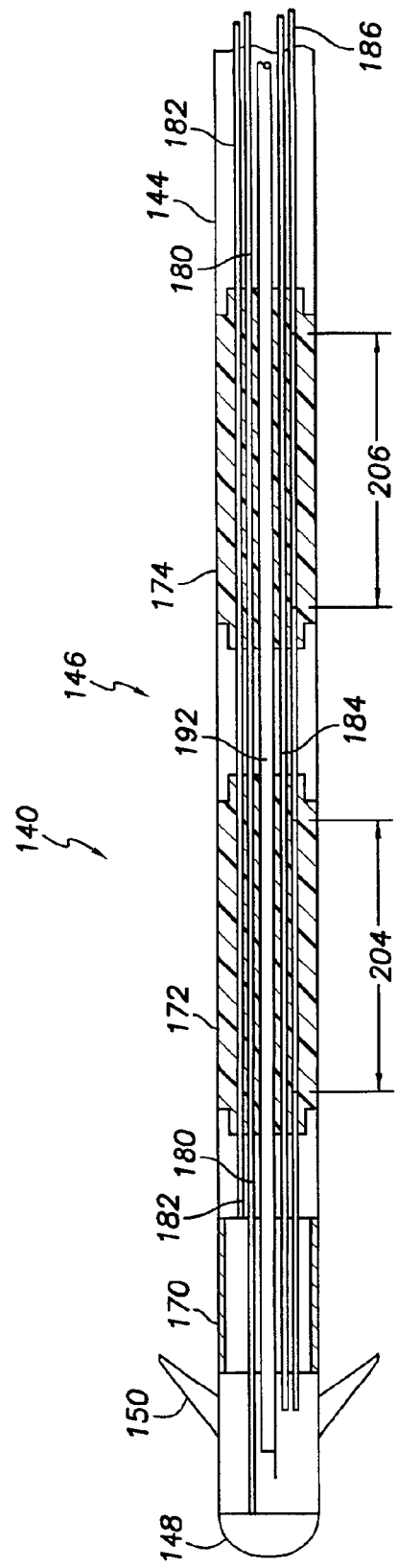
FIG. 28
FIG. 29

BODY IMPLANTABLE LEAD INCLUDING ONE OR MORE CONDUCTIVE POLYMER ELECTRODES AND METHODS FOR FABRICATING SAME

FIELD OF THE INVENTION

The present invention relates generally to body implantable leads. More particularly, the invention relates to body implantable, transvenous leads having one or more conductive polymer electrodes. The invention further relates to methods for fabricating such leads.

BACKGROUND OF THE INVENTION

Body implantable, transvenous leads form the electrical connection between a pulse generator such as a cardiac pacemaker and/or ICD and the heart tissue which is to be stimulated. The leads include a lead body comprising a tubular, flexible biocompatible, biostable insulative sheath or housing of silicone rubber, polyurethane or other suitable polymer. In a typical bipolar lead having a tip electrode and a ring sensing electrode, two coaxial coil conductors with insulation in between are carried within the insulative housing. One of the coil conductors connects the pulse generator with the tip electrode while the other coil conductor, somewhat shorter than the first conductor coil, connects the pulse generator with the ring sensing electrode positioned proximally of the tip electrode.

To reduce the outside diameter of the lead, lead bodies comprising multilumen housings have been developed. In place of coil conductors, such multilumen housings may contain multistrand cable conductors to connect the pulse generator at the proximal end of the lead with the tip and ring sensing electrodes at the distal end of the lead. In some existing multilumen lead body assemblies, a combination of a coil conductor and one or more cable conductors is utilized.

Transvenous leads often combine a cardioverting and/or defibrillating capability with the pacing and sensing functions. Thus, besides pacing and sensing electrodes, a transvenous type lead may include along its distal end portion one or more cardioverting and/or defibrillating electrodes for shocking selected tissue, for example, the tissue of the SVC and right or left ventricle.

One type of defibrillating electrode comprises a bare, that is, uninsulated, helically wound wire which relies on direct contact between the electrode and tissue or blood within or near the heart to deliver electrical energy to the heart. U.S. Pat. No. 5,431,681 discloses an example of this technology. Uninsulated, helical shocking coils tend to encourage tissue ingrowth as well as attachment of red blood cells and platelets (thrombus). Both of these conditions pose potentially serious risks to the patient. To address these problems, it is known to coat or otherwise cover an uninsulated helically wound transvenous shocking coil with polymeric material to minimize tissue ingrowth and/or inhibit the formation of thrombus at the shocking electrode. Typically, such polymeric coatings or coverings comprise porous, biocompatible insulating materials, such as PTFE, that become electrically conductive as body fluids penetrate the pores. Examples of patents disclosing such approaches to the problems of tissue ingrowth and thrombus formation include U.S. Pat. Nos. 5,090,422; 4,573,480; and 5,861,023.

Body implantable stimulation leads including electrodes made of conductive polymers are known. Thus, U.S. Pat. No. 5,476,496 discloses a bipolar body implantable pacing lead including inner and outer, coaxial coil conductors. The inner coil conductor is electrically connected to a pacing/sensing tip electrode at the distal extremity of the lead. The coils are electrically isolated from each other by a first insulating sleeve disposed between the inner and outer coil conductors. The outer coil conductor is enclosed within a second insulating sleeve. A portion of the second sleeve is made of a conductive polymer engaging the outer coil conductor so as to provide electrical contact therebetween. The conductive polymer portion of the second sleeve functions as the indifferent electrode of the pacing system. The indifferent electrode is relatively long so as to provide a large electrode surface area. Further, at least a part of the indifferent electrode is located outside the heart so as to prevent cardiac signals from being detected by the indifferent electrode since this would interfere with the interpretation of signals sensed by the tip electrode. The '496 patent does not deal with sensing or defibrillating electrodes. Given its length and its placement both inside and outside the heart, the conductive polymer electrode that is disclosed could not serve as a sensing or defibrillating electrode.

U.S. Pat. No. 3,815,611 discloses an isodiametric body implantable lead incorporating a proximal cardioverting electrode constructed of a conductive, flexible silicone rubber material. Details of the structure and fabrication of the cardioverting conductive polymer electrode are lacking; the electrode appears to comprise a thin sleeve enveloping an insulative silicone rubber casing molded about coil conductors. The conductor supplying electrical current to the conductive polymer sleeve appears to be attached to the sleeve at a confined junction or attachment point and it is doubtful that such an arrangement can provide sufficient charge/current to effectively and reliably terminate defibrillation.

The advantages of providing pacing therapies to the left side heart chambers and to both the right and left heart chambers are well established. For example, in four chamber pacing systems, four pacing leads, typically bipolar leads, are positioned for both pacing and sensing in the respective heart chambers. To provide left side stimulation and sensing, leads are transvenously implanted in the coronary sinus region, for example, in a vein such as the great vein or the left posterior ventricular (LPV) vein proximate the left ventricle of the heart. Such placement avoids the risks associated with implanting a lead directly within the left ventricle which can increase the potential for the formation of blood clots which may become dislodged and then carried to the brain where even a small embolism could cause a stroke. (As used herein, the phrase "coronary sinus region" refers to the coronary sinus, great cardiac vein, left marginal vein, left posterior ventricular vein, middle cardiac vein, and/or small cardiac vein or any other vein accessible by way of the coronary sinus.)

The tip electrode of a lead implanted in the coronary sinus region can pace and sense left side ventricular activity. When such a lead includes a ring sensing electrode proximal of the tip electrode and residing in the coronary sinus above the left ventricle closely adjacent to the left atrium of the heart, pacing and sensing of left atrial activity is made possible. Moreover, the lead may include one or more electrodes for the delivery of electrical shocks for terminating tachycardia and/or fibrillation. Such cardioverting and/or defibrillating electrodes may be used by themselves or can be combined with the aforementioned pacing and/or sensing electrodes.

The implantation of a lead through the coronary ostium and into the veins in the coronary sinus region is often difficult because of the extreme curvatures in the coronary vessels, their narrowness, anomalies in the vascular anatomy because of disease, and the number of veins which may communicate with the desired lead feed path. Some currently available leads, and particularly the distal end portions thereof, are too stiff to permit maneuvering of the distal end portion within the coronary vessels.

Thus, there is a need for improved body implantable leads that have the flexibility needed to enable the lead to be tracked through the coronary ostium and into the veins of the coronary sinus region for left side pacing, sensing and/or cardioversion/defibrillation. Conductive polymer electrodes for sensing, cardioversion, and defibrillation functions can provide the flexibility-necessary for difficult coronary sinus region placement.

SUMMARY OF THE INVENTION

In accordance with one, specific, exemplary embodiment of the invention, there is provided an implantable lead comprising a lead body having a proximal end portion and a distal end portion. The lead body includes a conductive polymer electrode disposed along the distal end portion of the lead body for performing one or more of the functions consisting of pacing, sensing, cardioversion and defibrillation. A cable conductor is contained within the lead body, the cable conductor coupling the proximal end portion of the lead body with the conductive polymer electrode, the conductive polymer electrode encapsulating the cable conductor and being in electrical contact therewith along the length of the conductive polymer electrode.

Pursuant to another specific, exemplary embodiment of the invention, there is provided an implantable lead comprising a lead body having a proximal end portion and a distal end portion, a first conductive polymer electrode being disposed along the distal end portion of the lead body for performing one or more of the functions consisting of pacing, sensing, cardioversion and defibrillation. A first cable conductor is contained within the lead body and extends from the proximal end portion into the distal end portion of the lead body, the conductive polymer electrode encapsulating the cable conductor and being in electrical contact therewith along the length of the conductive polymer electrode. The arrangement further includes a second conductive polymer electrode disposed along the distal end portion of the lead body for performing one or more of the functions of pacing, sensing, cardioversion and defibrillation, the second conductive polymer electrode being longitudinally spaced apart from the first conductive polymer electrode. A second cable conductor contained within the lead body extends from the proximal end portion into the distal end portion of the lead body, the second conductive polymer electrode encapsulating the second cable conductor and being in electrical contact therewith along the length of the second conductive polymer electrode.

In accordance with yet another specific, exemplary embodiment of the invention, there is provided a body implantable lead adapted to transmit electrical signals between a proximal end of the lead and a distal end portion of the lead, the distal end portion of the lead having a distal extremity including a tip electrode adapted to engage cardiac tissue and to electrically stimulate the tissue and/or sense electrical stimuli therefrom. The lead further comprises a first electrical conductor extending from a connector assembly at the proximal end of the lead, the first electrical conductor having a distal extremity electrically connected to the tip electrode. A second electrical conductor, electrically insulated from the first conductor, extends from the connector assembly at the proximal end of the lead into the distal end portion of the lead. A generally tubular, insulating housing of biocompatible, biostable polymer material extends between the proximal end and the distal end portion of the lead. The housing encloses the conductors except along an exposed section of the second conductor, the exposed section of the second conductor being disposed within the distal end portion of the lead. A conductive polymer electrode comprising a cardioverting and/or defibrillating electrode encapsulates the exposed section of the second conductor and is in electrical contact therewith along substantially the entire length of the exposed section.

An implantable lead in accordance with still another specific, exemplary embodiment of the invention includes a lead body having a proximal end portion and a distal end portion. The lead body comprises a tubular, insulative, multilumen housing including a conductive polymer electrode disposed within a window formed in the housing along the distal end portion of the lead body, the electrode performing one or more of the functions consisting of pacing, sensing, cardioversion and defibrillation. A conductor contained within one of the lumens of the multilumen housing couples the proximal end portion of the lead body with the conductive polymer electrode, the conductive polymer electrode encapsulating the conductor and being in electrical contact therewith along substantially the entire length of the conductive polymer electrode.

Still another specific, exemplary embodiment of the present invention comprises a body implantable lead adapted to transmit electrical signals between a proximal end of the lead and a distal end portion of the lead, the distal end portion of the lead including a tip electrode adapted to engage cardiac tissue and to electrically stimulate the tissue and/or sense electrical stimuli therefrom. The lead comprises a tip electrode conductor connecting the proximal end of the lead with the tip electrode and at least one additional electrical conductor extending from the proximal end of the lead into the distal end portion of the lead. The arrangement further includes a generally tubular, insulating, multilumen housing of biocompatible, biostable material extending between the proximal end and the distal end portion of the lead. The tip electrode conductor is contained within a first lumen of the multilumen housing and the at least one additional electrical conductor is contained within at least one of the remaining lumens of the multilumen housing. The housing encloses the at least one additional electrical conductor except along an exposed section thereof, the exposed section of the at least one additional conductor being disposed within the distal end portion of the lead. The lead further includes a conductive polymer electrode contained within a window formed in the multilumen housing, the electrode encapsulating the exposed section of the at least one additional conductor and being in electrical contact with the exposed section. The conductive polymer is adapted to engage cardiac tissue and to perform one or more of the functions consisting of pacing, sensing, cardioversion and defibrillation.

In accordance with yet another embodiment of the present invention, there is provided a body implantable lead suitable for electrically stimulating and/or sensing the tissue of the left side of the heart. The lead pursuant to this embodiment comprises a lead body having an isodiametric distal end portion configured to passively anchor the lead in the coronary sinus region of the heart, and a distal tip electrode adapted to be placed in a vessel in the coronary sinus region. At least one conductive polymer electrode adapted to perform one or more of the functions consisting of pacing, sensing, cardioversion and defibrillation is disposed along the distal end portion of the lead proximally of the tip electrode. The at least one conductive polymer electrode is so positioned along the distal end portion of the lead body as to be placed in a vessel in the coronary sinus region. A first electrical conductor within the lead body couples the tip electrode with a connector assembly at the proximal end of the lead body, and a second electrical conductor within the lead body couples the conductive polymer electrode with the connector assembly.

In accordance with another aspect of the invention, there is provided a method of fabricating a body implantable lead comprising the steps of providing an insulative housing containing at least one electrical conductor; removing one or more sections of the insulative housing along the distal end portion thereof to expose one or more sections of the electrical conductor; encapsulating the exposed section(s) of the electrical conductor in a conductive polymer in a plasticized, uncured or molten state, the conductive polymer being in electrical contact with the exposed section(s) of the electrical conductor; and curing or solidifying the conductive polymer.

There is also provided a method of fabricating a body implantable lead comprising the steps of placing at least two insulated, electrical conductors in side-by-side relationship; stripping the insulation from a section along the length of one of the at least two conductors; and molding a conductive polymer electrode about the at least two conductors so that the electrode is in electrical contact with substantially the entire length of the stripped section of the one conductor.

BRIEF DESCRIPTION OF THE DRAWINGS

The foregoing and other objects, features and advantages of the invention will become evident to those skilled in the art from the detailed description of the preferred embodiments, below, taken together with the accompanying drawings, in which:

FIG. 1 is a side view of a coaxial conductor coil pacing and cardioversion/defibrillating lead in accordance with a first embodiment of the invention including a lead body carrying a conductive polymer shocking electrode;

FIG. 2 is an axial cross section of the portion of the lead body of FIG. 1 carrying the conductive polymer shocking electrode;

FIG. 3 is a transverse cross section of the lead body of the first embodiment as seen along the line 3—3 in FIG. 2;

FIG. 4 is a side view, partly in cross section, of the portion of the lead body of FIGS. 1–3 carrying the conductive polymer shocking electrode, with the portion of the lead body shown within a compression mold for forming the conductive polymer shocking electrode;

FIG. 5 is a transverse cross section of the mold and lead body portion shown in FIG. 4, as seen along the line 5—5 in FIG. 4;

FIG. 6 is an axial cross section of a portion of a lead in accordance with a second embodiment of the invention, the lead of the second embodiment including an isodiametric lead body and conductive polymer shocking electrode carried by the lead body;

FIG. 7 is a side view, partly in cross section, of the portion of the lead body of FIG. 6 carrying the conductive polymer shocking electrode, the portion of the lead body being shown within a compression mold for forming the conductive polymer shocking electrode;

FIG. 8 is a perspective view, partly in phantom, of a portion of a lead in accordance with a third embodiment of the present invention, the lead including a trilumen lead body carrying a pair of cable conductors electrically connected to a conductive polymer shocking electrode encapsulating portions of the conductors exposed within a window formed in the lead body;

FIG. 9 is a transverse cross section of the lead body shown in FIG. 8 as seen along the line 9—9 in FIG. 8;

FIG. 13 is a perspective view, partly in phantom, of a lead in accordance with a fifth embodiment of the present invention, the lead including an isodiametric, trilumen lead body carrying a conductive polymer shocking electrode encapsulating portions of a pair of cable conductors exposed within a window formed in the lead body;

FIG. 14 is a transverse cross section of the lead body shown in FIG. 13 as seen along the line 14—14 in FIG. 13;

FIG. 17 is a perspective view of a portion of a lead in accordance with a sixth embodiment of the present invention, the lead including a trilumen lead body having a window adapted to be filled with a conductive polymer;

FIG. 18 is a transverse cross section of the lead shown in FIG. 17 as seen along the line 18—18 in FIG. 17;

FIG. 19 is a side view of a portion of a lead in accordance with a seventh embodiment of the invention in which a trilumen lead body includes three longitudinally spaced apart windows each adapted to receive conductive polymer;

FIGS. 20–22 are transverse cross section views of lead bodies including conductive polymer electrode windows having configurations in accordance with eighth, ninth and tenth embodiments of the invention;

FIG. 23 is a perspective view of a portion of a lead in accordance with an eleventh embodiment of the invention including a quad lumen lead body housing incorporating a conductive polymer electrode disposed within a helical window formed in the lead body;

FIGS. 24–26 are transverse cross section views of the lead shown in FIG. 23 as seen along the lines 24—24, 25—25 and 26—26, respectively, in FIG. 23;

FIG. 28 is a side view of a lead in accordance with a thirteenth embodiment of the present invention, the lead including an isodiametric, quad lumen lead body carrying a tip electrode, a sensing electrode and two conductive polymer cardioversion/defibrillating electrodes;

FIG. 29 is a side view, in cross section, of the distal end portion of the lead assembly of FIG. 28;

DESCRIPTION OF THE PREFERRED EMBODIMENTS

Figure 10:
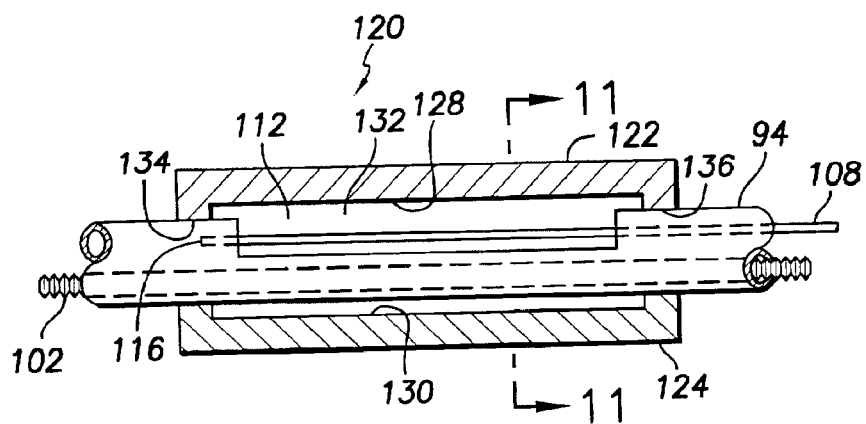
FIG. 10 is a side view, partly in cross section, of the portion of the lead body of FIGS. 8 and 9 carrying the conductive polymer shocking electrode, with the portion of the lead body shown within a compression mold for forming the conductive polymer shocking electrode.

The following description presents preferred embodiments of the invention representing the best mode contemplated for practicing the invention. This description is not to be taken in a limiting sense but is made merely for the purpose of describing the general principles of the invention whose scope is defined by the appended claims.

Although the conductive polymer electrodes of the invention will be described principally in the context of a cardioverting/defibrillating electrode, it will be evident to those skilled in the art that the teachings of the invention may be applied to other electrode structures, for example, sensing ring electrodes.

FIG. 1 shows in simplified, schematic form a passive-fixation endocardial, body implantable lead 10 in accordance with a first embodiment of the invention. The lead 10 includes a lead body 12 having a distal end portion 14 and a proximal end portion 16. The distal end portion 14 includes a tip electrode 18 and a conductive polymer cardioversion/defibrillating shocking electrode 20, hereinafter sometimes referred to simply as a defibrillating electrode. By way of example and not limitation, the distal end portion 14 of the lead body 12 may have a diameter of about 0.026 inch (2F) to about 0.131 inch (10F), with a diameter of about 0.079 (6F) being preferred, and the electrode 20 may have a diameter of about 0.091 inch (7F) and a length of about 2 inches. As is well known in the art, a lead of the type shown may further include a sensing electrode 21 in the form of a ring positioned proximally of the tip electrode. Such a ring sensing electrode may have a length of, for example, about 0.100 inch. The lead body includes an insulating sheath or housing 22 of a suitable insulative, biocompatible, biostable material such as, for example, silicone rubber or polyurethane, extending substantially the entire length of the lead body. The housing 22 includes along the distal end portion of the lead a plurality of rearwardly projecting tines 24 functioning, as is well know in the art, to interlock in the trabeculi within the heart and thereby prevent displacement of the distal end portion 14 once the lead is implanted. Although tines are the preferred anchoring means for purposes of the present invention, it will be understood by those skilled in the art that fins, a screw-in helix, or some other suitable anchoring means may be used instead, including one or more S-shaped bends along the distal end portion, without tines, for anchoring in the vessels of the coronary sinus region, as will be further described below in connection with the embodiment of FIG. 31.

The proximal end portion 16 includes a bifurcated connector assembly 26 for coupling the lead 10 to a pacemaker/defibrillator. The bifurcated connector assembly 26 comprises a first connector 28, which may conform to the DF-1 standard, for supplying electrical impulses to the defibrillating electrode 20, and a second connector 30, which may conform to the IS-1 standard, for connecting the pacemaker/defibrillator to the tip electrode 18 and sensing electrode 21. The second connector 30 includes a connector pin 32.

With reference now also to FIGS. 2 and 3, the connector pin 32 on the proximal end portion is hollow and is electrically coupled to the tip electrode 18 by means of an inner coil conductor 40 enclosed within the tubular housing 22. In accordance with well known implantation procedures, a stylet is passed through the hollow connector pin 32 and the central cavity or lumen 42 of the inner coil conductor 40 to enable the implanting physician to orient the distal end portion of the lead assembly and to thereby position the tip electrode under fluoroscopy to a desired location in the heart.

Where both pacing and sensing functions are performed by the tip electrode 18, the inner coil conductor 40 provides a bidirectional electrical transmission link between the pacemaker/defibrillator and the tip electrode 18. Where a ring sensing electrode such as the electrode 21 is utilized, a separate coil conductor (not shown) is incorporated in the lead 10 for connecting a terminal on the connector 30 with the sensing electrode.

Disposed coaxially about the inner coil conductor 40 is an insulating sleeve 44. Disposed about the outer surface of the insulating sleeve 44 is an outer coil conductor 46 connected at the proximal end thereof to the DF-1 connector 28 for delivering an electrical charge generated by the defibrillator to the defibrillating or shocking electrode 20.

As best seen in FIG. 2, a longitudinal section of the insulative housing 22 along the length of the distal end portion of the lead is removed so as to define a gap 50 through which a portion 52 of the outer coil conductor 46 is exposed. In accordance with one specific example of the invention, the gap 50 may have a length of about two inches. Formed about the exposed portion 52 of the outer coil conductor, in a manner to be described, is the conductive polymer defibrillation electrode 20. The conductive polymer defibrillation electrode 20 is in intimate electrical contact with the exposed portion 52 of the outer coil conductor 46 along substantially the entire length of the gap 50 in the housing 22. It will be seen that in the specific embodiment under consideration, the defibrillating electrode 20 has ends 54 and 56 overlapping with the insulative housing for a short distance at the distal and proximal extremities of the defibrillation electrode. Preferably, as seen in FIG. 2, the defibrillating coil conductor terminates at a distal extremity 58 just past the distal end 54 of the defribillating electrode 20.

As noted, in accordance with an aspect of the invention, the defibrillating electrode 20 comprises a conductive polymer. Such conductive polymers fall into two general categories: intrinsically conductive and conductor-filled. Intrinsically conductive polymers include polyacetylene, polypyrrole, and polyanaline, among others. Alternatively, conductor-filled polymers may include presently available materials approved for implantation such as silicone rubber with embedded metallic, carbon or graphite particles or powder. Silver filled silicone rubbers of the kind manufactured by NuSil or Specialty Silicone Products, modified so as to be approved for implantation, are of potential utility. An example is silver-coated, nickel-filled silicone rubber sold as NuSil R2637. This material, although not presently approved for medical device applications, offers the flexibility of silicone rubber and a conductance similar to MP35N, the current choice for pacemaker lead conductors.

With reference to FIGS. 4 and 5, there is shown in simplified form a compression mold 70 for forming in situ, the conductive polymer defibrillating electrode 20 about the exposed outer surface 52 of the outer coil conductor 46. Although compression molding is preferred because of its simplicity and low cost, it will be evident to those skilled in the art that other processes such as injection molding can be utilized instead. The compression mold 70 comprises two mold parts 72 and 74 internal recesses 76 and 78 respectively, the two parts together defining an internal cavity 80 within which the conductive polymer electrode is formed. The recess in one of the mold halves 72, 74 is loaded with plasticized uncured conductive polymer, for example, silicone, and the portion of the lead assembly including the exposed outer coil portion 52 is pressed into the recess. A close fitting mandrel must be placed within the lumen of the inner insulating sleeve 44 to prevent its collapse during molding. Plasticized, uncured conductive polymer is then pressed into the recess of the other mold half and the mold halves are then pressed and clamped together. The conductive polymer is heat cured at an elevated temperature, for example 300° F. for a period ranging from five to thirty minutes. After curing and separation of the mold halves, any excess polymer is cut away. After the molding step is complete, the inner coil conductor 40 is slid into the lumen of the inner insulative sleeve 44. Where the electrode 20 is made of a thermoplastic material such as filled polyurethane, the material is loaded in a molten state into the mold and allowed to solidify therein. Alternatively, a premolded insert could be placed in the mold cavities in the solid state, and allowed to flow into the final shape within the clamped and heated mold.

It will be seen that in the first embodiment of the invention, the conductive polymer defibrillating electrode 20 has an outer diameter slightly larger than the outer diameter of the insulative housing 22. Although a small difference in diameter can be tolerated, it is preferable to make the conductive polymer electrode the same diameter as that of the insulative housing to form an isodiametric lead body.

A portion of such as an isodiametric lead body 300, comprising a second embodiment of the invention, is shown in FIG. 6. As before, the lead body 300 comprises an insulative tubular housing 302; an inner coil 304 coupling a connector on the proximal end of the lead with a tip electrode; an insulating sleeve 306 disposed about the inner coil 304; and an outer coil 308 about the sleeve 306 coupling a connector on the proximal end of the lead with a conductive polymer defibrillating electrode 310. As before, the defibrillator electrode is in intimate electrical contact with an exposed portion 312 of the outer coil 308. The sole difference between the defibrillating electrode 310 of the second embodiment and the defibrillating electrode 20 of the first embodiment is that the outer diameter of the former is the same as that of the lead body housing 302.

FIG. 7 shows a compression mold 320 for forming in situ, the conductive polymer defibrillating electrode 310. The mold 320 is identical to the mold shown in FIGS. 4 and 5, including two mold parts 322 and 324 together defining an internal cylindrical cavity 326 within which the conductive polymer electrode 310 is formed. Pursuant to the second embodiment of the invention, the cylindrical cavity 326 has a diameter equal to that of the tubular housing 302.

FIGS. 8 and 9 show a portion of a body implantable endocardial lead assembly 90 in accordance with a third embodiment of the present invention. As in the first embodiment, the lead assembly 90 is adapted to transmit electrical signals between a proximal end portion (not shown) and a distal end portion a part 92 of which is shown in FIG. 8. As before, the distal end portion includes a distal extremity including a tip electrode (not shown) adapted to engage cardiac tissue and to electrically stimulate that tissue and/or sense electrical stimuli therefrom. The lead assembly 90 further includes a tubular trilumen housing 94 preferably fabricated of silicone rubber, polyurethane or other suitable biocompatible, biostable elastomer. The trilumen housing 94 defines three axially or longitudinally extending, parallel passages or lumens 96, 98 and 100 one of which (100) is larger than the other two and carries a preferably multistrand coil conductor 102 coupled between a hollow pin terminal at the proximal end of the lead assembly and the tip electrode. The hollow interior or lumen 104 of the coil conductor 102 provides access for a stylet used during lead implantation. The coil conductor 102 transmits electrical signals between the tip electrode and the pacemaker circuitry of a pacemaker/defibrillator; as noted, these electrical signals may comprise pacing stimuli to the heart tissue engaged by tip electrode as well as sensed electrical signals emanating from the heart.

The remaining two lumens 96 and 98 which, as indicated, are smaller than the lumen 100 enclosing the coil conductor 102, carry multistrand cables 106 and 108, respectively, connected via a contact at the proximal end of the lead assembly 90 to the defibrillator circuitry of the pacemaker/defibrillator, for carrying cardioversion and/or defibrillating electrical stimuli.

As explained in greater detail below, it will be appreciated that only one cable 106 or 108 may be used; one cable may be used to carry electrical signals to a ring sensing electrode while the other is used to provide current to the defibrillating electrode; two cables are preferred for redundancy and to provide additional current carrying capacity for the high energy shocking signals. It will also be evident that more than two cables may be utilized. For example, if three cables are incorporated in the lead assembly, a quad lumen housing can be employed. Further, those skilled in the pacing lead art will appreciate that one or more additional conductors may be carried by the tubular housing for conducting sensed electrical signals from the heart to the pulse generator. In such a case, in accordance with well known expedients in the art, the lead assembly may carry a ring sensing electrode disposed proximally of the tip electrode. Still further, it will be obvious that instead of cable conductors, small diameter, finely wound coil conductors may be used instead.

The distal end portion of the lead assembly 90 includes a longitudinally extending conductive polymer defibrillating electrode 110. The defibrillating electrode 110 is positioned proximally relative to the tip electrode (and a sensing ring electrode if one is provided) so as to make contact with the cardiac tissue within the superior vena cava (SVC), atrium, or the ventricle of the heart. As shown in FIG. 8, the tubular housing includes a longitudinally extending section or window 112 along which the two cables 106 and 108 are exposed. As best seen in FIG. 9, the depth of the window 112 is enough to expose the cables 106 and 108 but not the tip electrode coil conductor 102. By way of example and not limitation, the length of the removed or cutaway section 112 may be about 2 inches. If the cables 106 and 108 are insulated, they are stripped of their insulation along substantially the entire length of the cutaway section or window 112 of the tubular housing. The defibrillator electrode 110 envelops the bare sections of the exposed cables 106 and 108 and is in intimate electrical contact therewith along substantially the entire length of the window 112 so as to provide an ample charge/current pathway for the high energy defibrillating pulse from the cables to the tissue/blood that surrounds the defibrillating electrode. In the specific embodiment shown in FIG. 8, the defibrillating electrode 110 has an outer diameter slightly larger than the outer diameter of the tubular trilumen housing 94 but, as will be explained below, it will be evident that the defibrillating electrode can be made isodiametric with the tubular housing to facilitate passage of lead through the vein leading to the heart during implantation.

The two cables 106 and 108 terminate at ends 114 and 116, respectively, just distally of the shocking electrode 110. Alternatively, the cables can be extended distally and anchored within the distal extremity of the lead assembly for additional strength.

Figure 11:
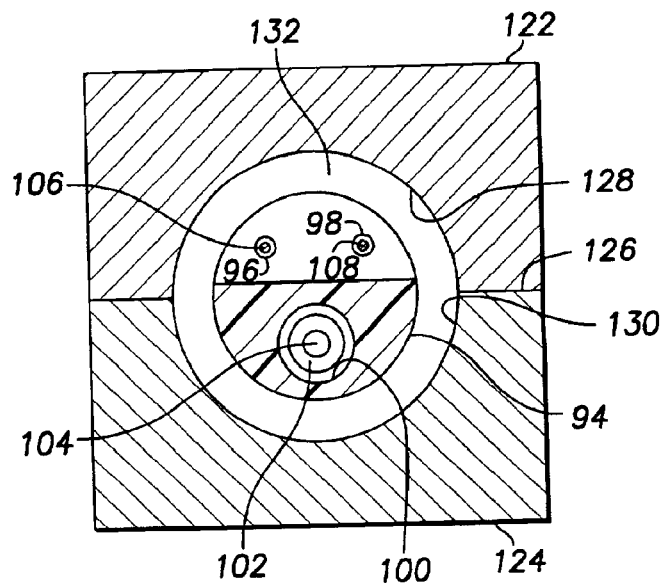
FIG. 11 is a transverse cross section of the apparatus and lead shown in FIG. 10 as seen along the line 11—11 in FIG. 10.

The conductive polymer electrode 110 may be fabricated using any known polymer forming process. As before, compression molding is preferred. A compression mold 120, shown schematically in FIGS. 10 and 11, comprises mold halves 122 and 124 adapted to be clamped together along a parting surface 126. The mold halves 122 and 124 define recesses 128 and 130 respectively, the recesses together forming a cylindrical cavity 132. Each end of the mold 120 includes an opening 134, 136 dimensioned to sealingly engage portions of the tubular housing 94 adjacent the window 112 of the housing when the mold halves are clamped together. The defibrillating electrode is formed by overloading the recess in one of the mold halves 122, 124 with plasticized, uncured conductive polymer and pressing the lead body into the loaded mold half with the cutaway section of the lead housing centered longitudinally within the mold half; a minimal amount of the uncured polymer will, of course, be squeezed out. Next, the other mold half is loaded with uncured, plasticized conductive polymer and the mold halves are then brought together along the parting surface 126 and clamped. Curing is effected by elevating the temperature of the mold to 300° F., for example, for a predetermined period which may vary from five to thirty minutes. After the conductive polymer has thus been cured the mold halves are separated and the excess polymer or flash is trimmed away. Where the electrode 110 is made of a thermoplastic material such as filled polyurethane, the material is loaded in a molten state into the mold and allowed to solidify therein. Alternatively, a premolded insert could be placed in the mold cavities in the solid state, and allowed to flow into the final shape within the clamped and heated mold.

Figure 12:
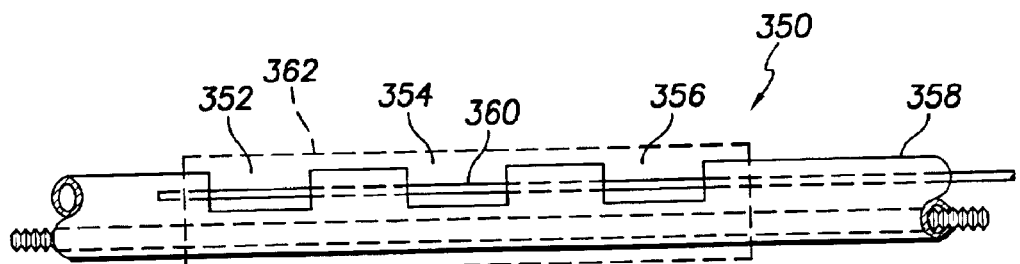
FIG. 12 is a side view of a portion of a lead in accordance with a fourth embodiment of the invention, the lead including a trilumen lead body carrying a pair of cable conductors electrically connected to a conductive polymer shocking electrode, the lead body having multiple windows formed therein for exposing sections of the conductor for encapsulation by the electrode.

FIG. 12 is a side view of a portion of a trilumen pacing and defibrillating lead 350 in accordance with a fourth embodiment of the invention identical in all respects to the third embodiment shown in FIG. 8 except that instead of a single cutaway section or window 112 as in FIG. 8, three cutaway sections or windows 352, 354 and 356 are formed in the trilumen housing 358 of the lead 350. Although the windows 352, 354 and 356 are preferably equally spaced and of equal length, it will be evident that this need not be the case; neither the spacings between the windows nor the lengths thereof need to be equal. Cables 360 are stripped of their insulation at least within each of the windows for electrical engagement with a conductive polymer defibrillating electrode 362, all as already explained. Stripping of the cable insulation only within the windows is preferred to better retain flexibility along the length of the defibrillating electrode.

Figure 15:
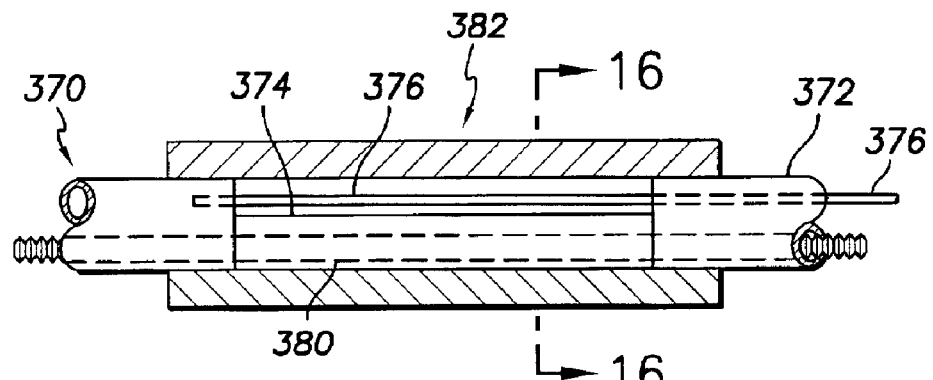
FIG. 15 is a side view, partly in cross section, of the portion of the lead body of FIGS. 13 and 14 carrying the conductive polymer shocking electrode, with the portion of the lead body shown within a compression mold for forming the conductive polymer shocking electrode.
Figure 16:
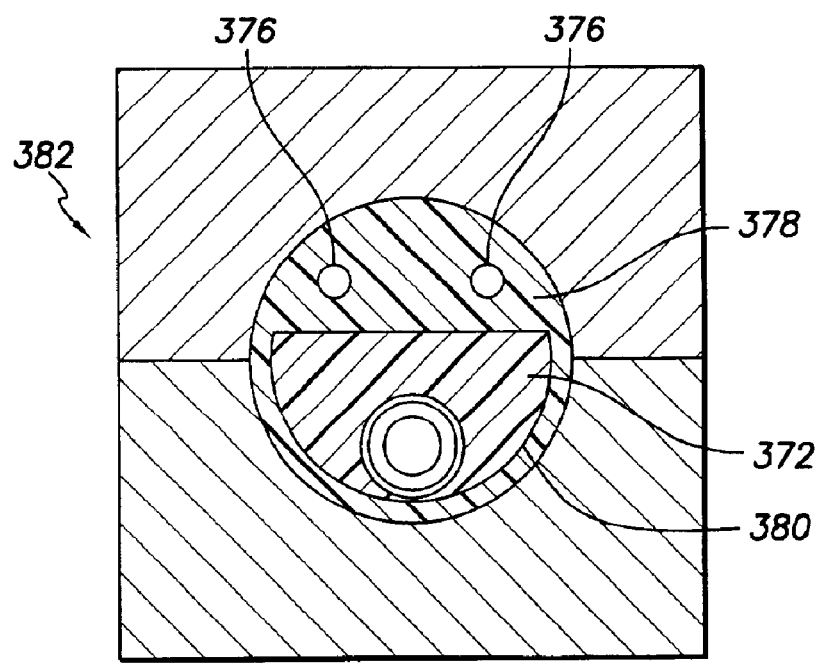
FIG. 16 is a transverse cross section of the mold and lead shown in FIG. 15 as seen along the line 16—16 in FIG. 15.
Figure 25:
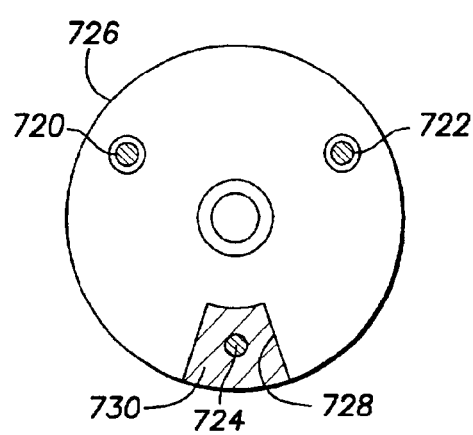
Figure 26:
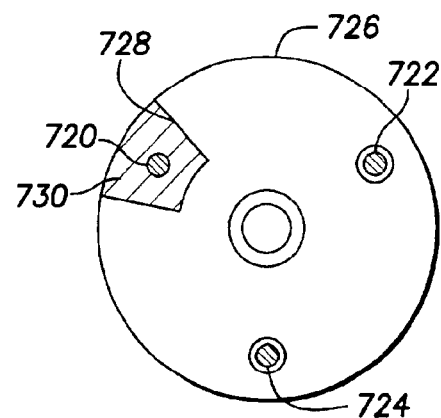

As in the case of the embodiment of FIG. 6, the trilumen lead body embodiment of FIGS. 8–11 may be provided with a conductive polymer defibrillating electrode that has the same outer diameter as that of the lead housing. In this connection, FIGS. 13 and 14 show a fifth embodiment of the invention comprising a lead body 370 including a trilumen housing 372 having a window 374 for exposing uninsulated lengths of one or more cable conductors 376 about which a conductive polymer electrode 378 is molded. To achieve the isodiametric structure desired, the outer diameter of the housing 372 is reduced at 380, that is, along the window 374. As before, a 2-part compression mold 382 (FIGS. 15 and 16) is preferably used to fabricate the conductive polymer electrode 378.

FIGS. 8–16 illustrate leads in accordance with the present invention that in each case comprises a multilumen housing including a pair of redundant cables (or small diameter, finely wound coils) electrically connecting a conductive polymer electrode encapsulating bare sections of the cables within one or more windows formed in the housing with a connector assembly at the proximal end of the lead. The window or windows extend in a longitudinal direction along the lead body and in each case the conductive polymer electrode extends about the entire circumference of the lead body housing. As shown in FIGS. 17 through 27, other variations are possible.

FIGS. 17–27 show variations of leads in accordance with the present invention including one or more windows each exposing a bare section of cable (or small diameter, finely wound coil conductor) for encapsulation within a conductive polymer electrode. In the earlier described embodiments of FIGS. 8–16, the conductive polymer electrodes have outer surfaces extending completely about the lead body. In the examples shown in FIGS. 17–27, as viewed in cross section, the windows receiving the conductive electrode polymer do not extend about the entire circumference of the lead body, that is, a window is cut out of the silicone housing which window does not extend around the entire circumference of the outer surface of the housing in order to expose either a cable, multiple cables or a coil. Uncured conductive silicone/polymer is then injected into the window, the portion of the lead body incorporating the filled window is enclosed in a clam shell mold and then heat cured. A thermoplastic conductive polymer may also be molded into the window by heating such polymer above its melting point.

FIGS. 17 and 18 show a first variation of the windows-type lead body comprising a sixth embodiment of the invention. The sixth embodiment has a lead body 600 including a trilumen, tubular housing 602 of silicone or the like including a pair of small lumens 604, 606 and a larger diameter lumen 608, the latter enclosing a coil conductor 622 coupling a tip electrode (not shown) with a contact on a connector assembly (not shown) at the proximal end of the lead. A single multistrand 612 cable (or small diameter coil conductor) is contained within the small lumen 604, while the other small lumen 606 may either be empty or contain a single cable 614 (or fine coil) coupling a sensor electrode, for example, on the distal end of the lead body with another contact on the connector assembly. A single window 616 comprising in cross section (FIG. 18) a quadrant of the tubular housing 602 has been removed so as to expose the single cable 612 which is then encapsulated by a conductive polymer electrode 618 in accordance with the methods already described. It will be seen that the outer curved surface 620 of the conductive polymer electrode occupies only a portion of the circumference of the housing 602 but is flush therewith so as to form an isodiametric lead structure. The remaining lumen 608 of the trilumen housing 602 may contain a coil conductor 622 connected to the tip electrode. Although a single, longitudinally extending window 616 is shown in FIG. 17, it will obvious that multiple, spaced apart, longitudinally extending windows each filled with conductive polymer encapsulating a bare section of the cable may be formed in the lead housing. FIG. 19 shows an example of such a multiple windows configuration, comprising a seventh embodiment including a tubular lead body housing 630 having removed therefrom three spaced apart windows 632, 634 and 636 each exposing a section of a cable conductor 638. As before, each of the windows 632, 634 and 636 is filled with a conductive polymer (not shown) to define three spaced apart electrode sections.

FIG. 20 is a cross section of an eighth embodiment comprising another variation of the window-type lead. The eighth embodiment comprises a tubular lead body housing 650 having a cylindrical outer surface 652. Instead of a quadrant being removed from the lead housing as in FIGS. 17 and 18, the window 654 in FIG. 20 comprises a generally wedge-shaped housing section subtending (in cross section) an angle less than 90°. The window 654 is filled with conductive polymer 656 whose outer, cylindrical surface 658 is coextensive with that of the tubular housing. Here again, either a single window or multiple, longitudinally spaced apart windows may be employed.

FIG. 21 is a cross section of a ninth embodiment having quad lumen lead body housing 670 including multiple, redundant cables 672, 674 and 676, each with its own wedge-shaped window 678, 680 and 682, respectively, that has been removed and filled with a conductive polymer. The three cables that are shown in FIG. 21 are all connected to the same contact on the connector assembly at the proximal end of the lead so as to provide the desired redundancy. In the example shown, the windows 678, 680 and 682 all have the same wedge-shaped geometry and are equiangularly disposed; it will be obvious that the windows, and hence the conductive polymer encapsulated therein may have different geometries and may be spaced at unequal angular intervals. Again, a single, conductive polymer-filled window may be employed for each cable, or each cable may be in contact with a plurality of conductive polymer electrodes filling longitudinally spaced windows. The multiple, redundant cables 672, 674 and 676, each encapsulated with a conductive polymer filling the associated window, allows a more uniform electrical charge distribution around the lead body.

FIG. 22 shows yet another variation of the windows-type lead comprising a tenth embodiment. This embodiment has a trilumen, insulative, tubular housing 690 including two longitudinally extending, arcuate passages or lumens 692 and 694 each enclosing a pair of cables or fine coils. One pair of cables 696, 698, enclosed within the lumen 692, may be connected to a sensing and/or stimulation electrode along the distal end of the lead body while the other pair of cables 700, 702 passes through a wedge-shaped window 704 removed from the housing 690. The use of two cables in each lumen provides the desired redundancy.

FIGS. 23–26 show an eleventh embodiment comprising a lead body 710 including an insulative, tubular, quad lumen housing 712 including three outer lumens 714, 716 and 718 occupied by cables 720, 722 and 724, respectively. Formed in the outer surface 726 of the housing is a helical groove or window 728 which in cross section has a wedge-shaped configuration and which intercepts the three lumens containing the cables. Because of the helical configuration of the window and the conductive polymer 730 contained therein, each of the cables intercepts the conductive polymer at longitudinally spaced apart locations, as seen in the cross sections of FIGS. 24–26.

Figure 27:
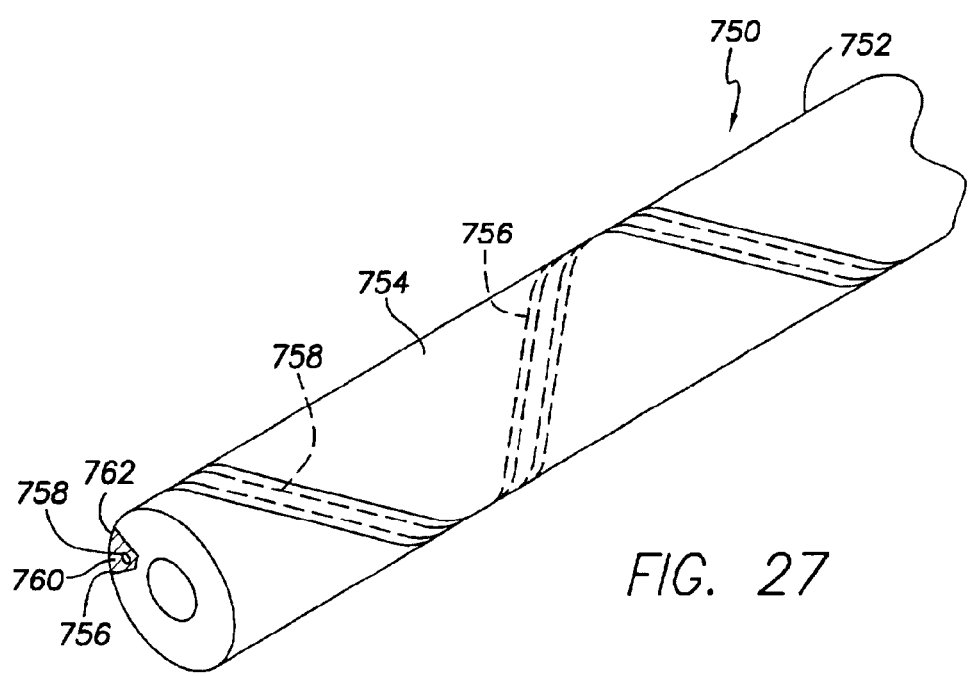
FIG. 27 is a perspective view of a portion of a lead in accordance with a twelfth embodiment of the invention having a helical window formed therein for receiving a conductive polymer electrode encapsulating a cable conductor extending along the helical window.

FIG. 27 shows a twelfth embodiment comprising a lead body 750 including an insulative housing 752 having an outer surface 754 with a helical groove or window 756 formed therein. Laid within the helical window 756 is a cable 758. The window 756 is filled with conductive polymer 760 which encapsulates the cable 758 and has an outer surface 762 flush with the outer-surface 754 of the lead body housing so as to form an isodiametric structure.

FIG. 28 depicts a body implantable endocardial lead 140 in accordance with a thirteenth embodiment of the invention. The lead 140 of the thirteenth embodiment includes a lead body 142 comprising a tubular housing 144 of silicone rubber, polyurethane or other suitable biocompatible, biostable insulative material. The lead body 142 is isodiametric and includes a distal end portion 146 terminating in a tip electrode 148. Projecting outwardly from the tubular housing along the distal end portion thereof are a plurality of tines 150 for engaging the heart tissue and urging the tip electrode 148 into contact with the endocardium. Alternatively, instead of tines, the distal end portion of the lead body 142 may have one or more bends formed therein for anchoring the distal end portion in a vessel of the coronary sinus region. The lead 140 further includes a proximal end portion 152 having a trifurcated connector assembly 154 including an SVC defibrillator connector 156, a ventricular defibrillator connector 158 and a pacing/sensing connector 160, the latter including a hollow connector pin 162.

Disposed proximally of the tip electrode 148 and tines 150 are a sensing ring electrode 170, a conductive polymer ventricular defibrillating electrode 172 and a conductive polymer SVC defibrillating electrode 174. As will be explained in connection with FIG. 47, the tip, sensing and ventricular defibrillating electrodes 148,170 and 172 may be positioned along the length of the lead body so that when the lead body is implanted at its destination, they make contact with cardiotissue within the ventricle while the SVC defibrillating electrode 174 is positioned to contact the tissue of the atrium and the SVC. By way of example and not limitation, the electrode 172 may have a length of 5–6 cm, the electrode 174 may have a length of 7–8 cm, and the electrodes 172 and 174 may be separated by a distance of 7–16 cm.

Figure 30:
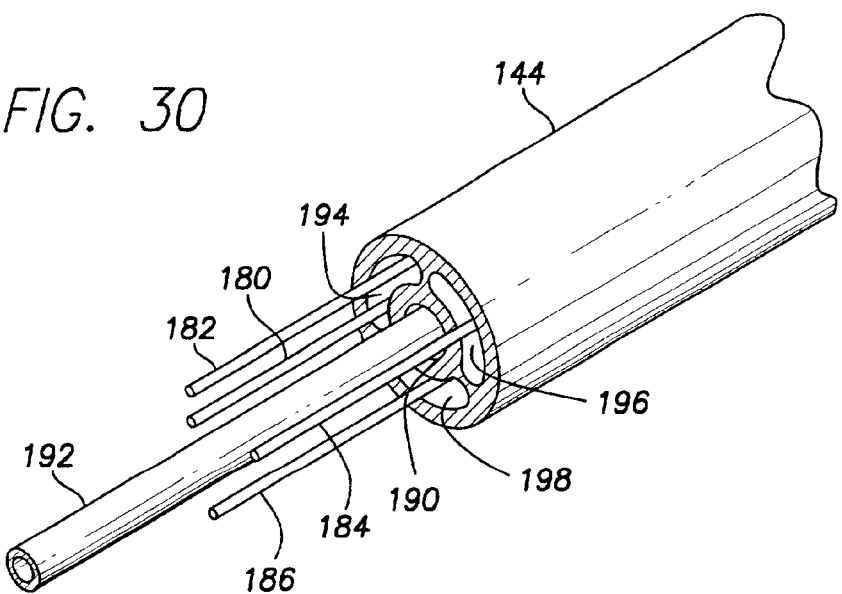
FIG. 30 is a perspective view of a portion of the quad lumen lead body of FIGS. 28 and 29.

As shown in FIGS. 29 and 30, the housing 140 contains four conductors 180, 182, 184 and 186 coupling the tip, sensing, ventricular defibrillating and SVC defibrillating electrodes 148, 170, 172 and 174 to the connectors 156, 158 and 160 at the proximal portion of the lead assembly. Although the conductors may comprise small diameter, finely wound coil conductors, cable conductors, and particularly multistrand cable conductors, are preferred.

As best seen in FIG. 30, the tubular housing 144 comprises a quad lumen structure including a central, longitudinally extending lumen 190 containing a thin wall, tubular PTFE liner 192 and three lumens 194, 196 and 198 each having an arcuate configuration in cross section surrounding the central lumen 190. The central PTFE liner 192 provides a passage for a stylet used during implantation to position the distal end portion of the lead assembly within the heart.

As seen in FIG. 30, two of the cables, for example, the cables 180 and 182, occupy and share the arcuate lumen 194; in this example, each of the two remaining cables 184 and 186 occupy one of the remaining two arcuate lumens 196 and 198.

The conductive polymer ventricular and SVC defibrillating electrodes 172 and 174 are molded about the cable conductors 184 and 186 in a manner to be described. The insulation on the cable conductor 184 supplying the ventricular defibrillating electrode is stripped along a length 204 and substantially the entire length of the cable conductor portion so exposed is in intimate electrical contact with the ventricular defibrillating electrode 172. Similarly, the insulation on the cable conductor 186 supplying the SVC defibrillating electrode is stripped along a length 206 and substantially the entire length of the cable conductor portion so exposed is in intimate electrical contact with the SVC defibrillating electrode 174.

Figure 31:
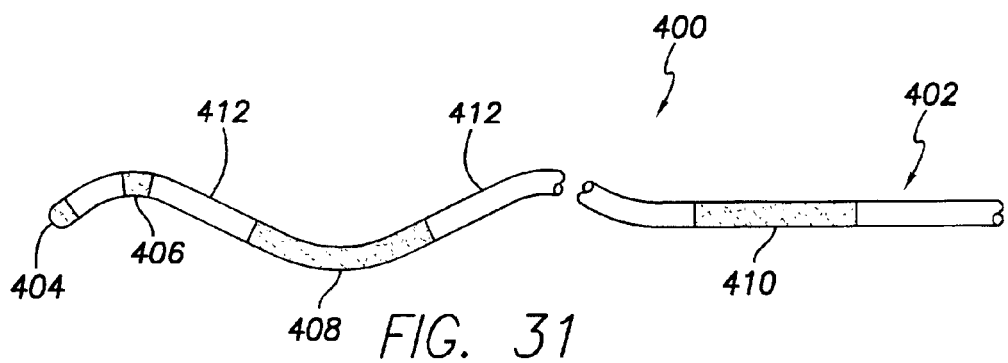
FIG. 31 is a side view of the distal end portion of a lead in accordance with a fourteenth embodiment of the invention, the lead being particularly useful for implantation in the coronary venous system of the heart.

FIG. 31 shows the distal end portion of a body implantable endocardial lead 400 in accordance with a fourteenth embodiment. The lead 400 includes an isodiametric lead body 402, identical to that of the thirteenth embodiment shown in FIGS. 28–30 except that the lead body 402 is particularly configured for implantation in the coronary sinus region of the heart for left side pacing, sensing and defibrillation. Like the thirteenth embodiment, the lead body 402 includes a tip electrode 404, a sensing ring electrode 406 (either metal or conductive polymer), a first or distal conductive polymer defibrillating electrode 408 and a second or proximal conductive polymer defibrillating electrode 410. As will be explained, the tip and ring sensing electrodes 404 and 406 and the first conductive polymer defibrillating electrode 408 may be implanted, by way of example, at a site within the left posterior ventricle (LPV) vein. In this case, the second or proximal conductive polymer defibrillating electrode 410 is positioned along the length of the lead body to contact a wall of the SVC (with a spacing of, for example, 13–20 cm between the electrodes 408 and 410) or, alternatively, closer to the first or distal conductive polymer defibrillating electrode 408 so as to be implantable within the coronary sinus region.

The distal end portion of the lead body 402 includes a passive fixation means to help anchor the distal end portion within a vessel in the coronary sinus region. The passive fixation or anchoring means may comprise one or more S-shaped humps, spirals, bends or other configurations of the distal end portion of the lead body 402. In the specific exemplary form of the invention shown in FIG. 31, the distal end portion of the lead body 402 has two S-shaped bends 412 so that when the distal end portion of the lead body is in place within a coronary vessel there will be contact between the bends and the inner wall of the vessel so as to create frictional forces sufficient to anchor the lead and prevent its displacement or dislodgment. The passive fixation means may further comprise a single or a plurality of soft, flexible protuberances that also tend to fix the distal end portion of the lead body 402 in the target coronary vein. In either case, such passive fixation means anchors the lead against the vessel wall. The passive fixation means can further include texturization of the distal end portion of the lead body to promote rapid blood clotting and resulting fibrotic tissue growth about the distal end portion to further help anchor that portion in place.

The outside diameter of the distal end portion may range from 0.026 inch (2F) to 0.091 inch (7F). As before, the sensing ring electrode 406 may have a length of about 0.10 inch and each of the conductive polymer defibrillating electrodes may have a length of about two inches. With such a small diameter, together with the use of conductive polymer electrodes, a thin flexible lead body is provided that can be readily delivered to a left side coronary vessel in the coronary sinus region through the SVC and via the coronary os and sinus.

Figure 32:
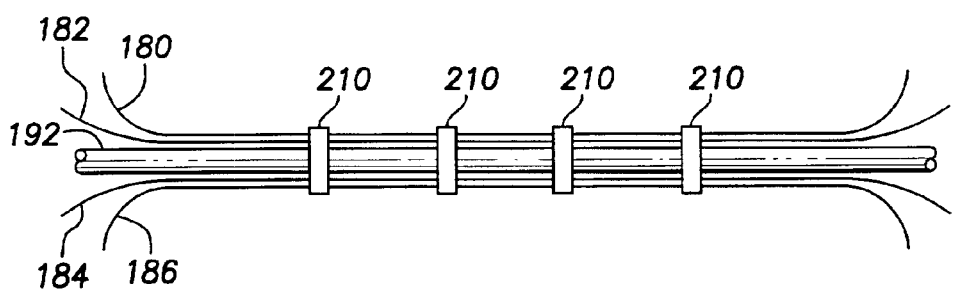
FIGS. 32–39 show the various stages in preparing a lead assembly in accordance with the thirteenth and fourteenth embodiments shown in FIGS. 28 and 31.
Figure 33:
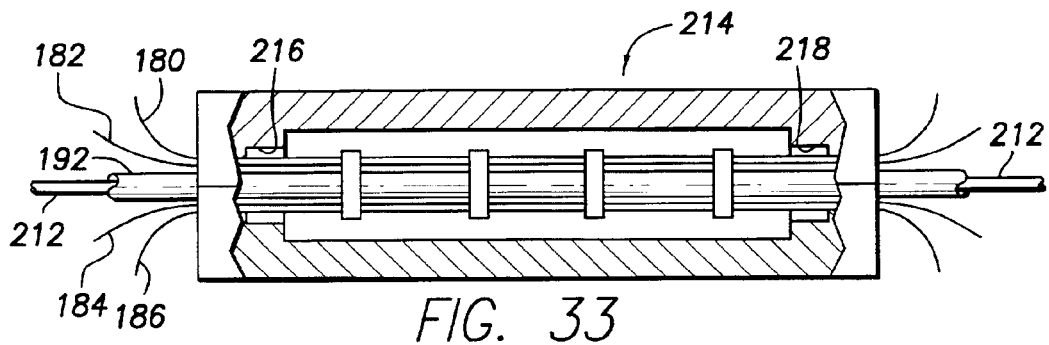
Figure 34:
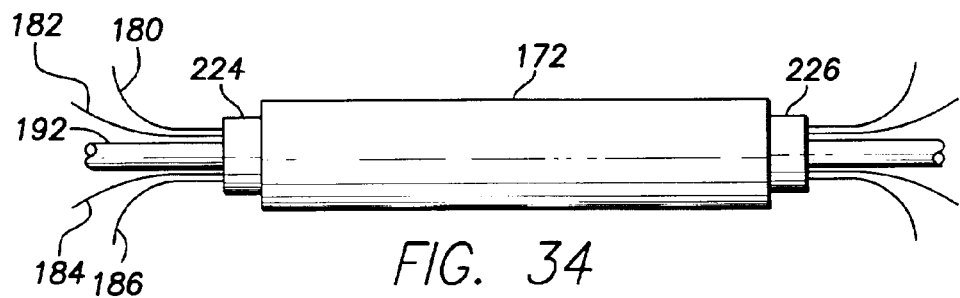

With reference to FIGS. 32–39, using the conductive polymer ventricular defibrillating electrode of the embodiment of FIGS. 28–30 as an example, fabrication of the electrodes will now be explained. The four cables 180, 182, 184 and 186 and the tubular PTFE liner 192 are grouped together as shown in FIG. 32. The insulation on the cable 184 supplying the ventricular defibrillating electrode is removed along about a two inch length. Small rings 210 of silicone may be placed around the cable/PTFE liner bundle to hold these elements together. A close fitting mandrel 212 is inserted in the PTFE liner 192 to prevent its collapse during the molding process (FIG. 33). Conductive polymer is then compression molded around the cable/PTFE liner bundle using a mold 214 as already described except modified to include reduced diameter shoulders 216 and 218 on the ends. (FIG. 34.) As noted, the conductive polymer will be in intimate electrical contact with the bare portion of the cable conductor 184.

Figure 35:
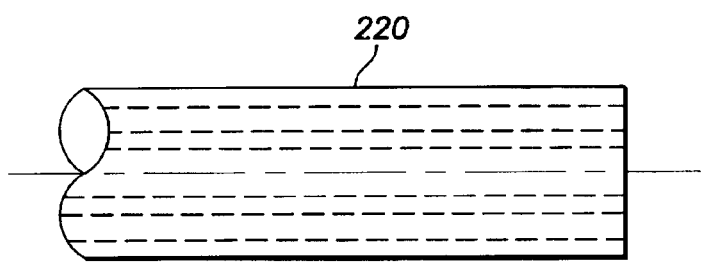
Figure 36:
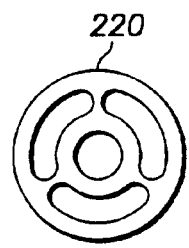
Figure 37:
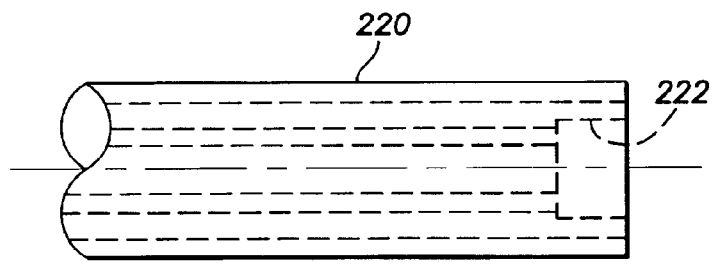
Figure 38:
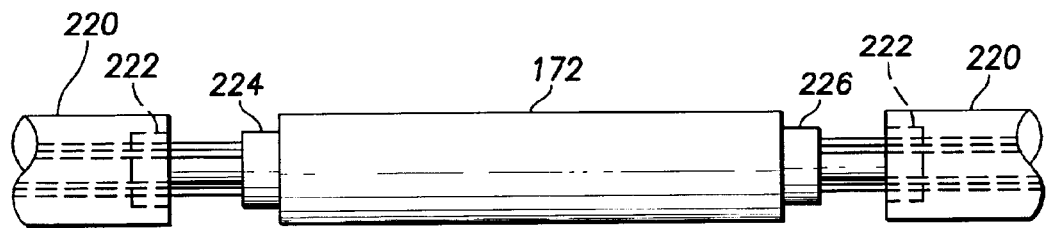
Figure 39:
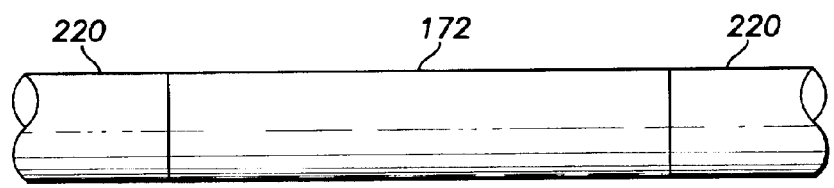

FIGS. 35 and 36 show side and end views, respectively, of a length 220 of the quad lumen housing 144. An end portion 222 of the length of the quad lumen tubular housing is cored out to a depth of approximately ⅛ inch, as shown in FIG. 37. Two such housing lengths are so prepared. Next, the cables and PTFE liner are slid into the lumens of the two lengths of the quad tubular housing. (FIG. 38.) The reduced diameter ends 224, 226 of the molded conductive polymer electrode are inserted into the cored out end portions. Silicone RTV (room temperature vulcanizing) adhesive is used to bond the reduced diameter ends of the conductive polymer electrode to the adjoining lengths of the tubular housing. The result is an isodiametric shocking electrode and lead body (FIG. 39). The foregoing steps are repeated to create the conductive polymer SVC defibrillating electrode 174. In the examples illustrated in FIGS. 28–31, the ring sensing electrode is made of conductive metal. However, it will be obvious that the sensing ring electrodes may be made of conductive polymer using the fabrication steps outlined above.

Figure 40:
FIGS. 40–45 show portions of cable conductors whose surfaces are provided with various area-increasing structures for enhancing the bond and mechanical interlock between the cable conductors and the conductive polymer electrode material encapsulating the conductors.
Figure 41:
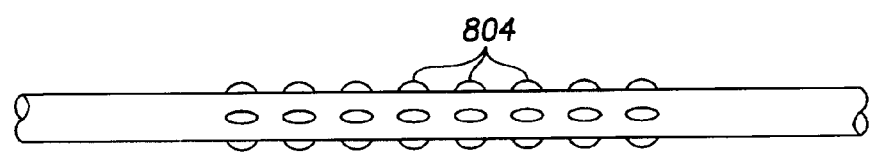
Figure 42:
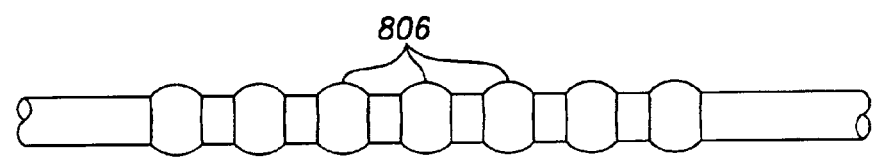
Figure 43:
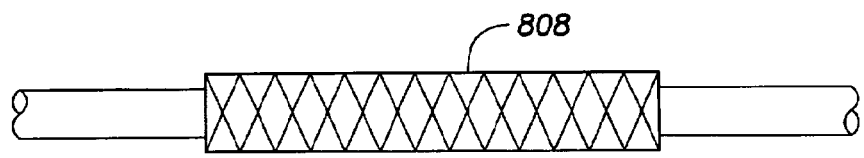
Figure 44:
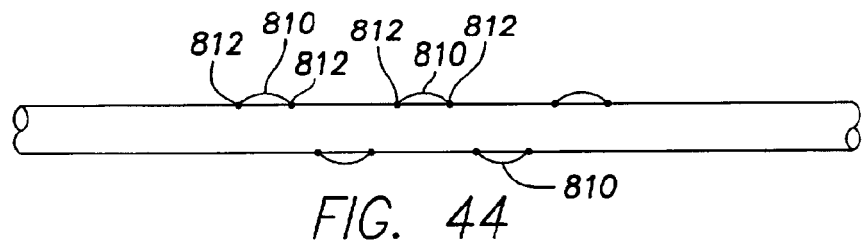
Figure 45:
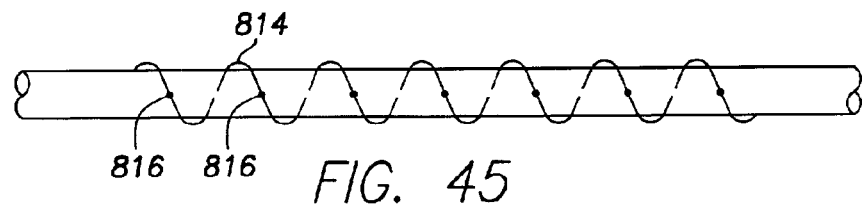

In FIGS. 8–39, cables having plain, bare surfaces at least within the confines of each the window are used and these will suffice in most instances to provide a sufficiently firm bond between the cable surface and the encapsulating conductive polymer. To enhance the bond and provide an additional mechanical interlock between a cable and the conductive polymer, the surface area of the cable may be increased along the section thereof to be bonded to the conductive polymer. For example, the surface 800 of a section of cable 802 to be bonded may be knurled or otherwise roughened (FIG. 40), or rolled, stamped, compressed, or otherwise mechanically treated to form bumps or bulges 804 or other projections in the surface of the cable. (See FIG. 41.) Conductive or nonconductive beads 806 may be attached to the surface of the cable at spaced apart locations by welding or other bonding process. (See FIG. 42.) Still further, the section of the cable to be encapsulated by the conductive polymer may be enveloped in a mesh 808, such as superelastic metal mesh, welded at spaced apart points to the cable section. (See FIG. 43.) Still further, individual wire loops 810 spaced apart along the length of the cable section may be welded at their ends 812 to the cable. (See FIG. 44.) Yet another embodiment, shown in FIG. 45, comprises a wire 814 wound around the cable section and welded thereto at spaced apart points 816.

Figure 46:
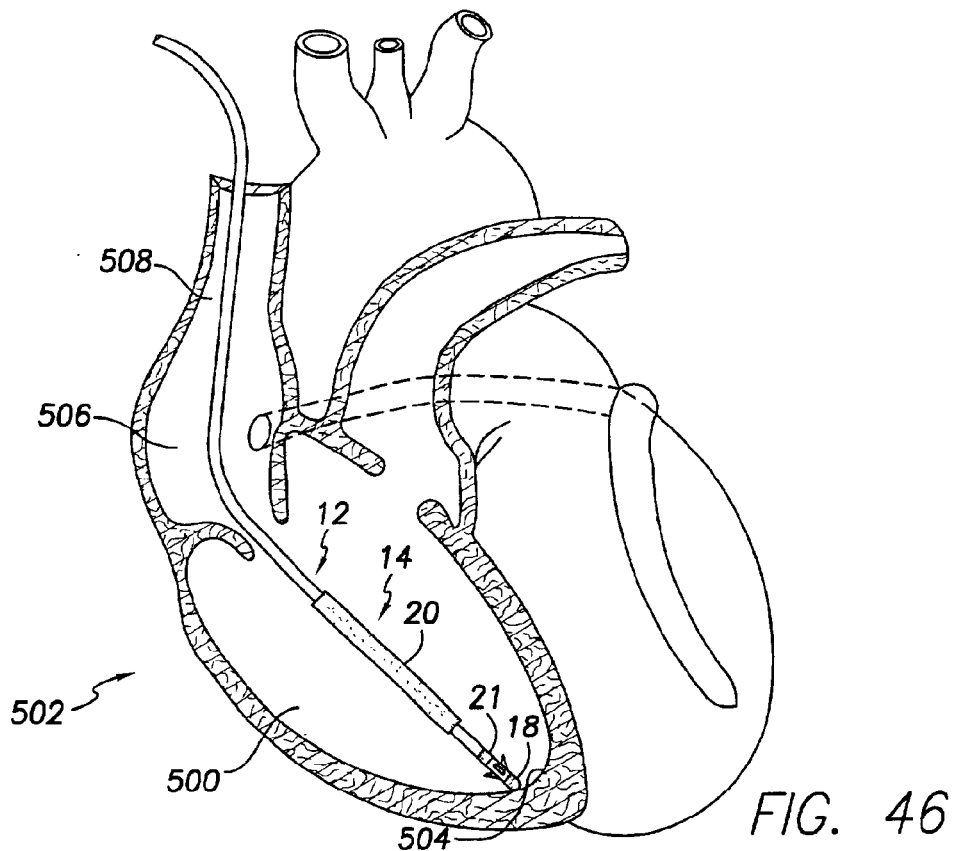
FIG. 46 is a perspective view of the human heart illustrating the lead of the first embodiment (FIG. 1) in its final position, with the tip electrode, the sensing electrode, and the conductive polymer shocking electrode at implantation sites within the right ventricle of the heart.

Referring now to FIG. 46, the distal end portion 14 of the lead 10 of FIG. 1 is shown in place at an implantation site within the right ventricle 500 of a heart 502, with the tip electrode 18 and ring sensing electrode 21 positioned approximately at the apex 504 of the right ventricle. In the specific example shown in FIG. 46, the conductive polymer defibrillating electrode 20 also resides at an implantation site within the right ventricle 500. It will be appreciated that the conductive polymer defibrillation electrode 20 may be positioned along the length of the lead body 12 relative to the tip electrode 18 so that it will be positioned within the right atrium 506 or within the SVC 508 of the heart 502.

Figure 47:
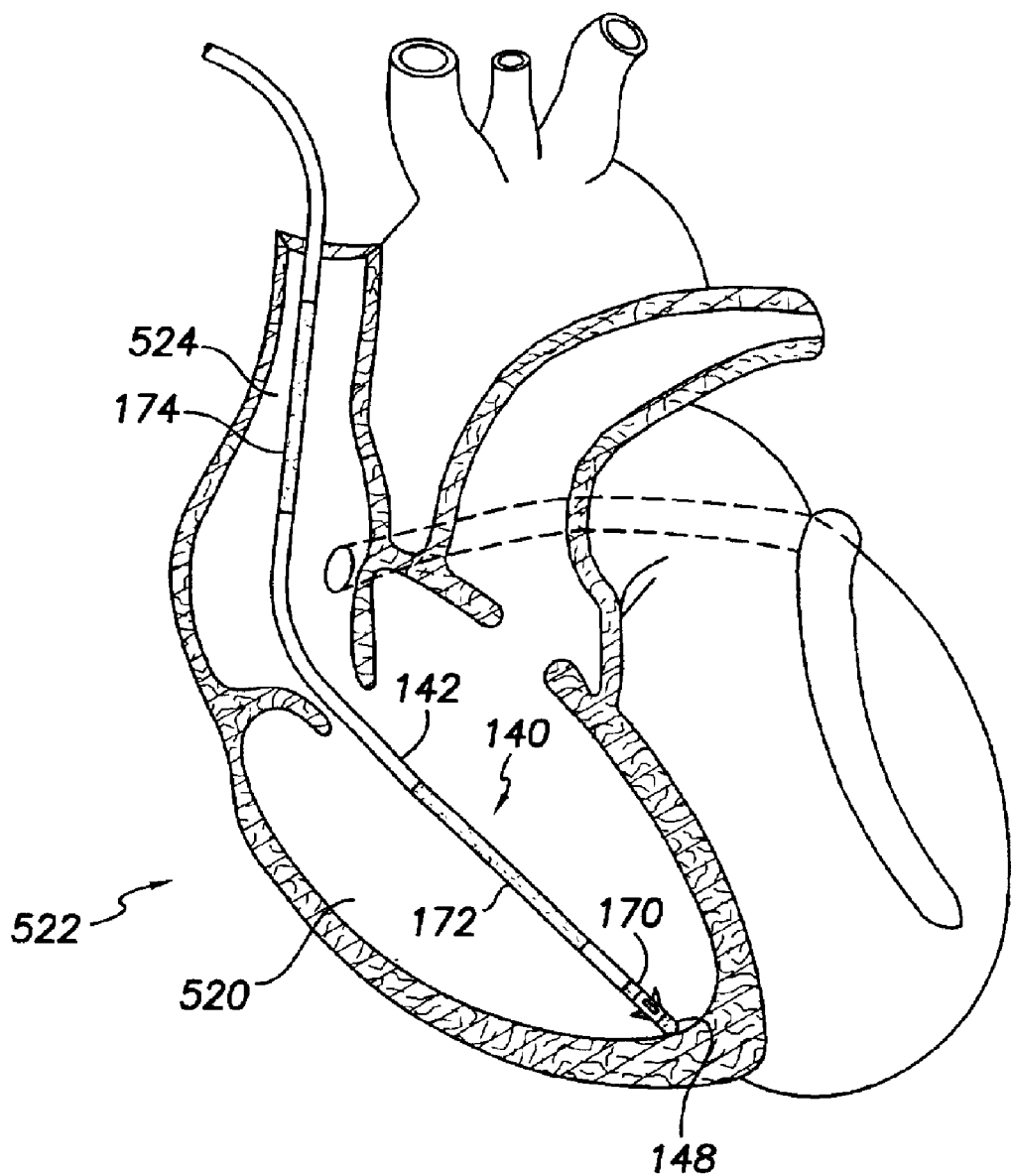
FIG. 47 is a perspective view of the human heart illustrating the lead of the thirteenth embodiment (FIG. 28) in its final position, with the tip electrode, the sensing electrode, and the distal conductive polymer shocking electrode at implantation sites within the right ventricle of the heart, and the proximal conductive polymer shocking electrode at an implantation site within the SVC of the heart.

FIG. 47 shows the distal end portion 146 of the lead 140 (FIG. 28) with the tip electrode 148, ring sensing electrode 170, and distal conductive polymer defibrillating electrode 172 disposed at their implantation sites within the right ventricle 520 of the heart 522. The proximal conductive polymer defibrillating electrode 174 is positioned along the length of the lead body 142 relative to the distal conductive polymer defibrillating electrode 172 so as to be positioned within the SVC 524. In both FIGS. 46 and 47, anchoring is provided by tines which become entangled in the trabeculi within the heart.

Figure 48:
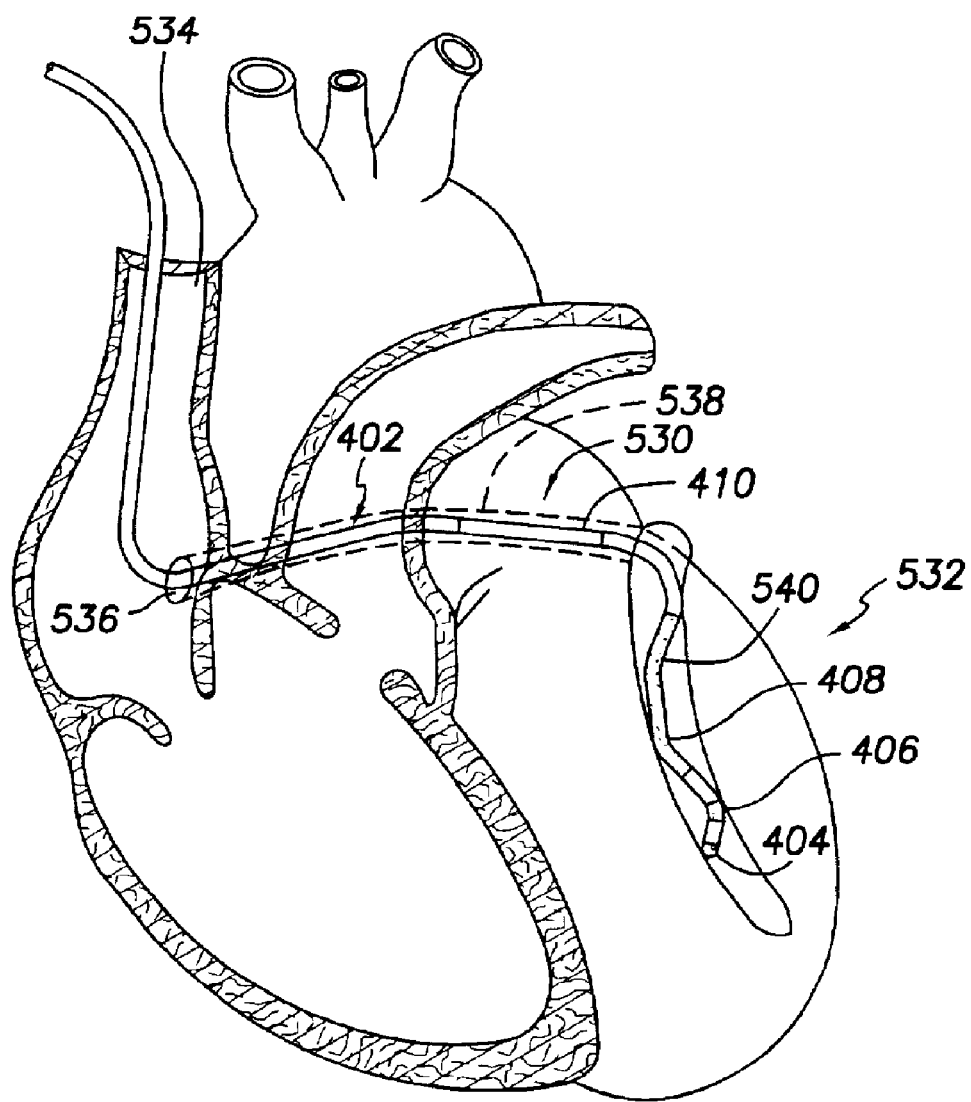
FIG. 48 is a perspective view of the human heart illustrating the lead of the fourteenth embodiment (FIG. 31) in its final position, with the tip electrode, the sensing electrode, and the conductive polymer shocking electrode at implantation sites within the coronary sinus region of the heart.

In accordance with another example, illustrated in FIG. 48, a lead 400 in accordance with the teachings of FIG. 31 is shown with the tip, ring and defibrillating electrodes 404, 406, 408 and 410 positioned within the coronary sinus region 530 of the heart 532 for left side stimulation and sensing. FIG. 48 shows the distal end portion of the lead body 402 passed through the SVC 534, the coronary os 536, the coronary sinus 538 and into the left posterior ventricle (LPV) vein 540, in accordance with this specific example. Further, the tip electrode 404, ring sensing electrode 406 and distal conductive polymer defibrillating electrode 408 are shown positioned within the LPV vein 540 while, in the example under consideration, the proximal conductive polymer defibrillating electrode 410 is shown positioned within the coronary sinus 538.

Figure 49:
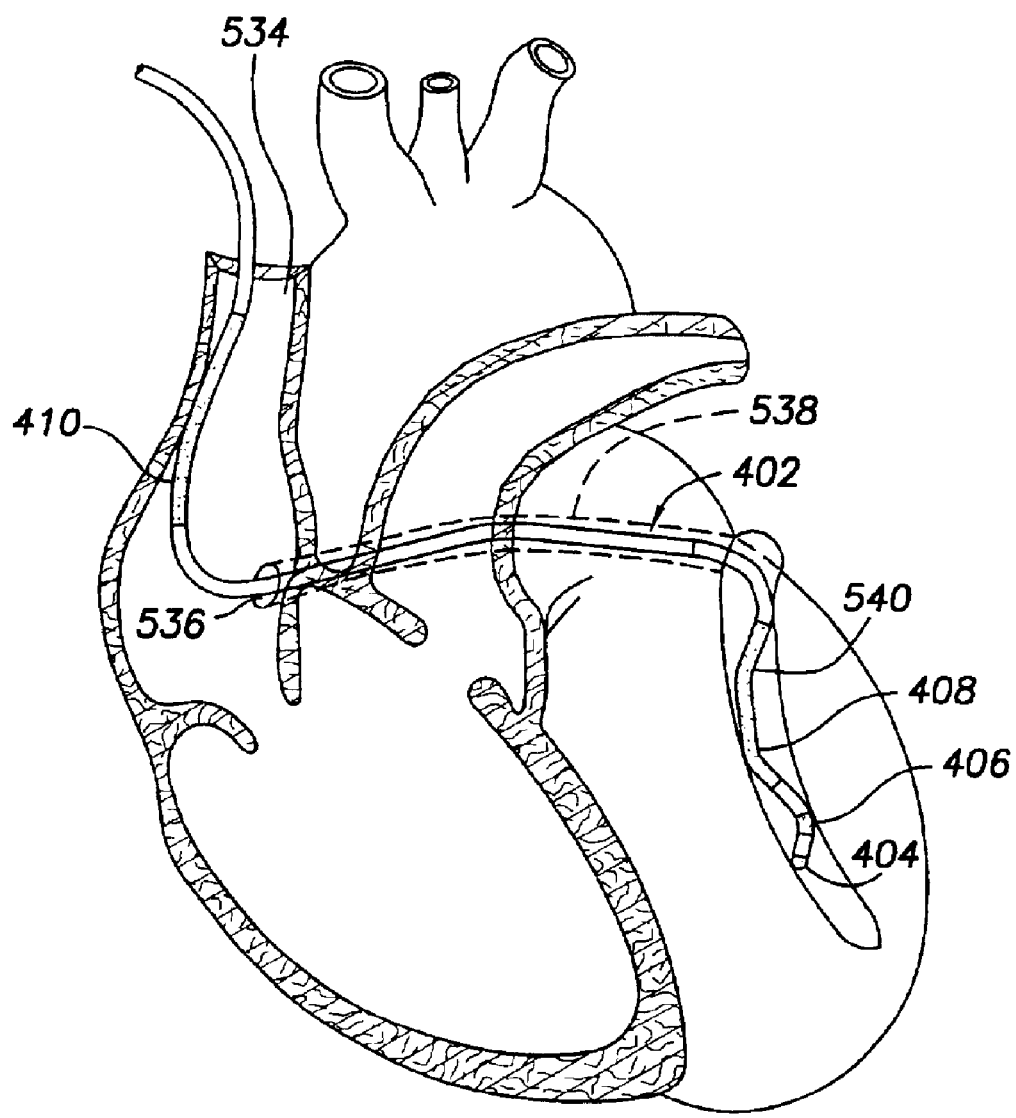
FIG. 49 is a perspective view of the human heart illustrating a variation of the lead of the fourteenth embodiment (FIG. 31) in its final position, with the tip electrode, the sensing electrode, and the distal conductive polymer shocking electrode at implantation sites within the coronary sinus region of the heart, and the proximal conductive polymer shocking electrode at an implantation site within the SVC of the heart.

FIG. 49 shows another example of the implantation of leads in accordance with the invention. FIG. 49 shows a variation of the distal end portion of the lead body 402 of FIG. 31. As was the case in connection with FIG. 48, the tip electrode 404, ring sensing electrode 406 and distal conductive polymer defibrillating electrode 408 are shown residing within the LPV vein 540. The proximal conductive polymer defibrillating electrode 410, however, is disposed along the length of the lead body 402 so that it resides within the SVC 534.

Figure 50:
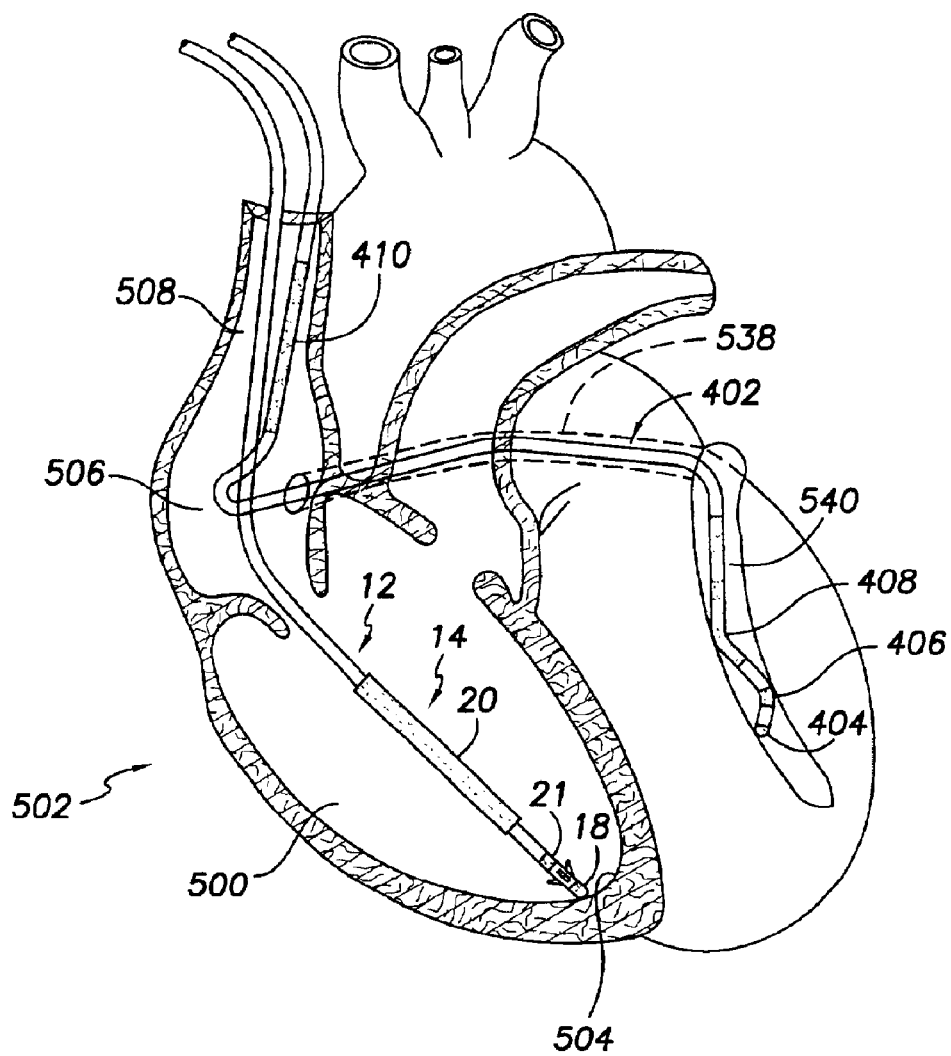
FIGS. 50 and 51 are perspective views of a human heart illustrating leads in accordance with the invention implanted to provide both right and left side shock impulses.
Figure 51:
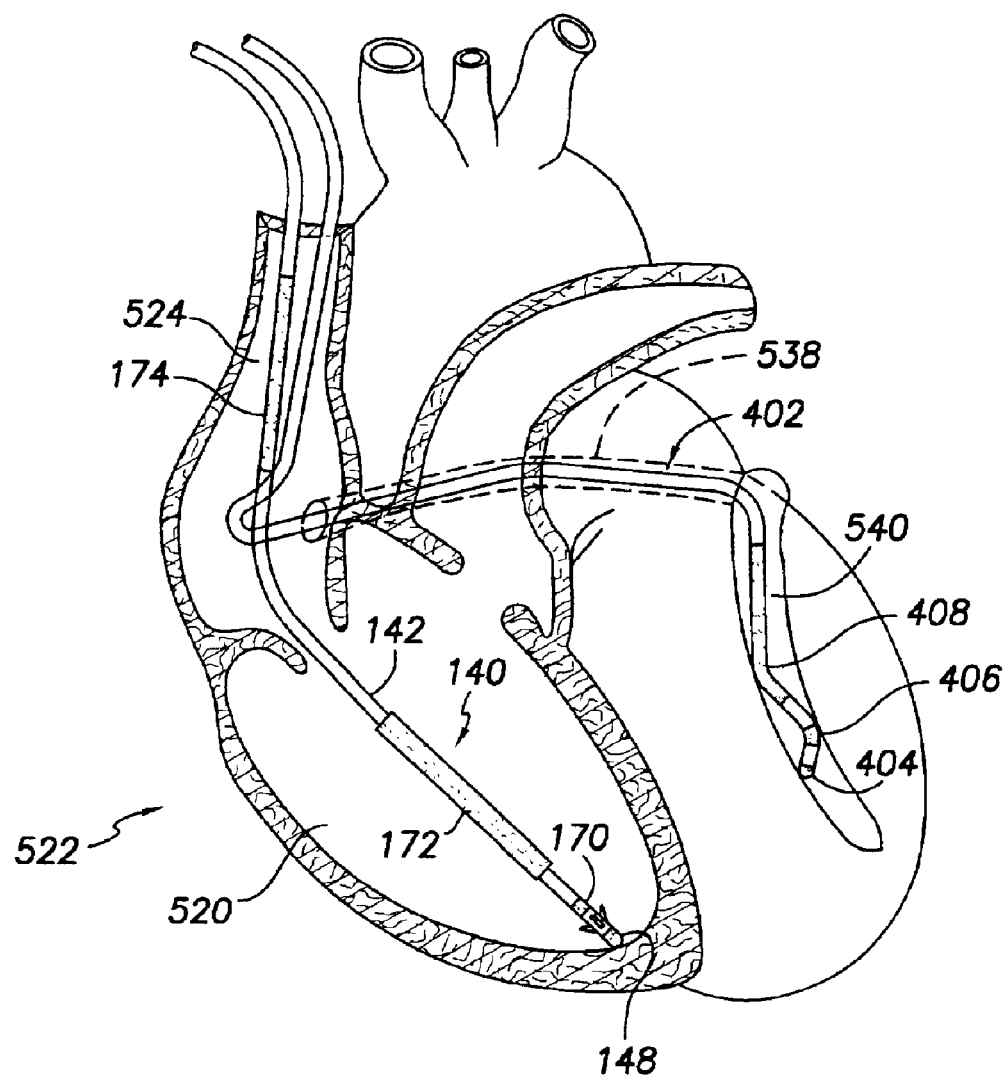

FIGS. 50 and 51 show combinations of right and left side leads in accordance with previously described embodiments providing for SVC cardioversion/defibrillation. Thus, the dual lead system of FIG. 50 combines the right side lead shown in FIG. 46 with the left side lead of FIG. 49. Accordingly, in the dual lead system of FIG. 50, the SVC cardioversion/defibrillating conductive polymer electrode, namely, electrode 410, is carried on the left side lead. The reference numerals used in FIG. 50 are the same as those used in FIGS. 46 and 49. In contrast, the dual lead system of FIG. 51 combines the right side lead of FIG. 47 which lead carries the SVC cardioversion/defibrillating electrode 174, with the left side lead of FIG. 49 without the SVC cardioversion/defibrillating electrode 410. Again, the reference numerals in FIG. 51 are the same as those previously used.

It will be evident that many variations of leads in accordance with the teaching of the invention are made possible for both right side and left side stimulation and sensing or combinations thereof, and the lead configurations and placements shown in FIGS. 46–51 are examples only, and by no means exhaustive.

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

What is claimed is:

1. An implantable lead comprising:
   a lead body having a proximal end portion and a distal end portion, the lead body including a conductive polymer electrode disposed along the distal end portion of the lead body for performing one or more of the functions consisting of pacing, sensing, cardioversion and defibrillation; and
   a conductor contained within the lead body, the conductor coupling the proximal end portion of the lead body with the conductive polymer electrode, the conductive polymer electrode encapsulating the conductor and being in electrical contact therewith along the length of the conductive polymer electrode, wherein the portion of the conductor encapsulated by the conductive polymer electrode includes area-increasing structure for enhancing the bond between the electrode and the conductor.

2. The lead of claim 1 in which:
   the conductive polymer electrode is disposed within a window formed in the lead body.

3. The lead of claim 2 in which:
   the window and the conductive polymer electrode disposed therein extend helically about the lead body.

4. The lead of claim 3 in which:
   the cable conductor extends longitudinally along the lead body and intercepts the helical conductive polymer electrode at longitudinally spaced apart points along the lead body.

5. The lead of claim 4 further including:

at least one additional cable conductor, redundant with the first mentioned cable conductor, contained within the lead body, the at least one additional cable conductor extending longitudinally along the lead body and intercepting the helical conductive polymer electrode at longitudinally spaced apart points along the lead body.

6. The lead of claim 5 in which:

the lead body comprises a multilumen housing, the first mentioned cable being contained within a first one of the lumens of the multilumen housing and the at least one additional cable conductor being contained within a second one of the lumens of the multilumen housing.

7. The lead of claim 5 in which:

the lead body comprises a multilumen housing, the first mentioned cable and the at least one additional cable conductor being contained within one of the lumens of the multilumen housing.

8. The lead of claim 3 in which:

the cable conductor is encapsulated within the helically extending conductive polymer electrode and follows the helical path thereof.

9. The lead of claim 2 in which:

the distal end portion of the lead body is isodiametric.

10. The lead of claim 2 in which:

the distal end portion of the lead body has an outer circumferential surface, the window extending about a portion of the outer circumferential surface.

11. The lead of claim 1 further including:

at least one additional cable conductor, redundant with the first mentioned cable conductor, contained within the lead body, the conductive polymer electrode encapsulating the at least one additional cable conductor along the length of the electrode.

12. The lead of claim 11 in which:

the lead body comprises a multilumen housing, the first mentioned cable being contained within a first one of the lumens of the multilumen housing and the at least one additional cable conductor being contained within a second one of the lumens of the multilumen housing.

13. The lead of claim 11 in which:

the lead body comprises a multilumen housing, the first mentioned cable and the at least one additional cable conductor being contained within one of the lumens of the multilumen housing.

14. The lead of claim 1 in which:

the area-increasing structure is selected from the group consisting of a roughened surface of the cable conductor, a knurled surface of the cable conductor, projections extending from a surface of the cable conductor, beads attached to a surface of the cable conductor, mesh attached to a surface of the cable conductor, longitudinally spaced apart wire loops attached to a surface of the cable conductor, and wire wound around and attached to a surface of the cable conductor.

15. The lead of claim 1 in which:

the conductive polymer electrode comprises at least two electrode sections disposed within a corresponding number of windows formed in the lead body and spaced apart along the length thereof.

16. The lead of claim 1 in which:

the conductive polymer comprises a polymer formulated to be intrinsically conductive.

17. The lead of claim 16 in which:

the conductive polymer is selected from the group consisting of polyacetylene, polypyrrole, polyaniline, polythiophene, fluorophenyl thiophene, polyphenylene vinylene, polyphenylene sulfide, polynaphthalene, and polyphenylene.

18. The lead of claim 1 in which:

the conductive polymer comprises an insulating, biocompatible polymer having conductive particles dispersed therein.

19. The lead of claim 18 in which:

the insulating polymer is selected from the group consisting of silicone rubber, polyurethane, and styrene-ethylene-butylene-styrene block polymer.

20. The lead of claim 18 in which:

the conductive particles comprise particles selected from the group consisting of silver, stainless steel, iridium, silver-coated nickel, carbon black, graphite, tantalum, palladium, titanium, platinum, gold, MP35N, fullerines, and carbon nanotubes.

21. The lead of claim 1 in which:

the conductive polymer electrode comprises a molded structure.

22. The lead of claim 1 in which:

a second conductive polymer electrode disposed along the distal end portion of the lead body for performing one or more of the functions of pacing, sensing, cardioversion and defibrillation, the second conductive polymer electrode being longitudinally spaced apart from the first mentioned conductive polymer electrode; and a second cable conductor contained within the lead body and coupling the proximal end portion of the lead body with the second conductive polymer electrode, the second conductive polymer electrode encapsulating the second cable conductor and being in electrical contact therewith along the length of the second conductive polymer electrode.

23. The lead of claim 22 in which:

the distal end portion of the lead body is adapted for implantation within the right side of a heart, wherein the first mentioned conductive polymer electrode is positioned along the length of the distal end portion of the lead body to deliver electrical stimuli to the tissue of the right ventricle of the heart, and the second conductive polymer electrode is positioned along the length of the distal end portion of the lead body to deliver electrical stimuli to the tissue of the superior vena cava of the heart.

24. The lead of claim 22 in which:

the distal end portion of the lead body is adapted for left side implantation, wherein the first mentioned conductive polymer electrode is positioned along the length of the distal end portion of the lead body to deliver electrical stimuli to the wall of a vessel in the coronary sinus region of the heart, and the second conductive polymer electrode is positioned along the length of the distal end portion of the lead body to deliver electrical stimuli to the tissue of the superior vena cava of the heart.

25. The lead of claim 22 in which:

the distal end portion of the lead body is adapted for left side implantation, wherein the first mentioned conductive polymer electrode is positioned along the length of the distal end portion of the lead body to deliver electrical stimuli to the coronary sinus of the heart, and the second conductive polymer electrode is positioned along the length of the distal end portion of the lead body to deliver electrical stimuli to a vein overlying the left side of the heart.

26. The lead of claim 22 in which:
the lead body includes a multilumen housing, a first one of the lumens of the housing containing the first mentioned cable conductor and a second one of the lumens containing the second cable conductor.

27. The lead of claim 26 in which:
the housing includes a third lumen, the third lumen containing a lining extending from the proximal end portion of the lead body to the distal end portion thereof, the lining passing through the lengths of the first and the second conductive polymer electrodes and being encapsulated thereby, the lining being adapted to guide a stylet during implantation of the lead.

28. An implantable lead comprising:
a lead body having a proximal end portion and a distal end portion, the lead body comprising a tubular, insulative, multilumen housing including a conductive polymer electrode disposed within a window formed in the housing along the distal end portion of the lead body, the electrode performing one or more of the functions consisting of pacing, sensing, cardioversion and defibrillation; and
a conductor contained within one of the lumens of the multilumen housing, the conductor coupling the proximal end portion of the lead body with the conductive polymer electrode, the conductive polymer electrode encapsulating the conductor and being in electrical contact therewith along substantially the entire length of the conductive polymer electrode, wherein the portion of the conductor encapsulated by the conductive polymer electrode includes area-increasing structure for enhancing the bond between the electrode and the conductor.

29. The lead of claim 28 in which:
the conductor comprises a cable conductor.

30. The lead of claim 28 which:
the conductor comprises a coil conductor.

31. The lead of claim 28 in which:
the distal end portion of the lead body is isodiametric.

32. The lead of claim 28 in which:
the distal end portion of the lead body has an outer circumferential surface, the window extending about a portion of the outer circumferential surface.

33. The lead of claim 28 further including:
at least one additional conductor, redundant with the first mentioned conductor, contained within the lumen of the multilumen housing, the conductive polymer electrode encapsulating the at least one additional conductor along substantially the entire length of the electrode.

34. The lead of claim 28 further including:
at least one additional conductor, redundant with the first mentioned conductor, contained within another one of the lumens of the multilumen housing, the conductive polymer electrode encapsulating the at least one additional conductor along substantially the entire length of the electrode.

35. The lead of claim 28 in which:
the window and the conductive polymer electrode disposed therein extend helically about the lead body.

36. The lead of claim 35 in which:
the conductor is encapsulated within the helically extending conductive polymer electrode and follows the helical path thereof.

37. The lead of claim 28 in which:
the area-increasing structure is selected from the group consisting of a roughened surface of the conductor, a knurled surface of the conductor, projections extending from a surface of the conductor, beads attached to a surface of the conductor, mesh attached to a surface of the conductor, longitudinally spaced apart wire loops attached to a surface of the conductor, and wire wound around and attached to a surface of the conductor.

38. The lead of claim 28 in which:
the conductive polymer electrode comprises at least two electrode sections disposed within a corresponding number of windows formed in the housing and spaced apart along the length thereof.

39. The lead of claim 28 in which:
the conductive polymer comprises a polymer formulated to be intrinsically conductive.

40. The lead of claim 39 in which:
the conductive polymer is selected from the group consisting of polyacetylene, polypyrrole, polyaniline, polythiophene, fluorophenyl thiophene, polyphenylene vinylene, polyphenylene sulfide, polynaphthalene, and polyphenylene.

41. The lead of claim 28 in which:
the conductive polymer comprises an insulating, biocompatible polymer having conductive particles dispersed therein.

42. The lead of claim 41 in which:
the insulating polymer is selected from the group consisting of silicone rubber, polyurethane, and styrene-ethylene-butylene-styrene block polymer.

43. The lead of claim 41 in which:
the conductive particles comprise particles selected from the group consisting of silver, stainless steel, iridium, silver-coated nickel, carbon black, graphite, tantalum, palladium, titanium, platinum, gold, MP35N, fullerines, and carbon nanotubes.

44. The lead of claim 28 in which:
the conductive polymer electrode comprises a molded structure.

45. The lead of claim 28 which includes:
a second conductive polymer electrode disposed along the distal end portion of the lead body for performing one or more of the functions of pacing, sensing, cardioversion and defibrillation; and
a second conductor contained within the housing and extending from the proximal end portion of the lead body into the distal end portion of the lead body, the second conductive polymer electrode encapsulating the second conductor and being in electrical contact therewith along substantially the entire length of the second conductive polymer electrode.

46. The lead of claim 45 in which:
the distal end portion of the lead body is adapted for implantation within the right side of a heart, wherein the first mentioned conductive polymer electrode is positioned along the length of the distal end portion of the lead body to deliver electrical stimuli to the tissue of the right ventricle of the heart, and the second conductive polymer electrode is positioned along the length of the distal end portion of the lead body to deliver electrical stimuli to the tissue of the superior vena cava of the heart.

47. The lead of claim 45 in which:
the distal end portion of the lead body is adapted for left side implantation, wherein the first mentioned conductive polymer electrode is positioned along the length of the distal end portion of the lead body to deliver electrical stimuli to the wall of a vessel in the coronary sinus region of the heart, and the second conductive polymer electrode is positioned along the length of the distal end portion of the lead body to deliver electrical stimuli to the tissue of the superior vena cava of the heart.

48. The lead of claim 45 in which:

the distal end portion of the lead body is adapted for left side implantation, wherein the first mentioned conductive polymer electrode is positioned along the length of the distal end portion of the lead body to deliver electrical stimuli to the coronary sinus of the heart, and the second conductive polymer electrode is positioned along the length of the distal end portion of the lead body to deliver electrical stimuli to a vein overlying the left side of the heart.

49. A body implantable lead adapted to transmit electrical signals between a proximal end of the lead and a distal end portion of the lead, the distal end portion of the lead having a distal extremity including a tip electrode adapted to engage cardiac tissue and to electrically stimulate the tissue and/or sense electrical stimuli therefrom, the lead comprising:

a first electrical conductor extending from a connector assembly at the proximal end of the lead, the first electrical conductor having a distal extremity electrically connected to the tip electrode;

a second electrical conductor, electrically insulated from the first conductor, extending from the connector assembly at the proximal end of the lead into the distal end portion of the lead;

a generally tubular, insulating housing of biocompatible, biostable polymer material extending between the proximal end and the distal end portion of the lead and enclosing the conductors except along an exposed section of the second conductor, the exposed section of the second conductor being disposed within the distal end portion of the lead; and a conductive polymer electrode encapsulating the exposed section of the second conductor and being in electrical contact therewith along substantially the entire length of the exposed section, the conductive polymer electrode comprising a cardioverting and/or defibrillating electrode, wherein the portion of the conductor encapsulated by the conductive polymer electrode includes area-increasing structure for enhancing the bond between the electrode and the conductor.

50. The lead of claim 49 in which:

the conductive polymer electrode is positioned along the length of the distal end portion of the lead to deliver cardioverting and/or defibrillating electrical stimuli to the tissue of the superior vena cava.

51. The lead of claim 49 in which:

the conductive polymer electrode is positioned along the length of the distal end portion of the lead to deliver cardioverting and/or defibrillating electrical stimuli to the coronary sinus.

52. The lead of claim 49 in which:

the conductive polymer electrode is positioned along the length of the distal end portion of the lead to deliver cardioverting and/or defibrillating electrical stimuli to a vein overlying the left side of the heart.

53. The lead of claim 49 in which:

the conductive polymer electrode is positioned along the length of the distal end portion of the lead to deliver cardioverting and/or defibrillating electrical stimuli to the tissue of a ventricle of the heart.

54. The lead of claim 53 in which:

the conductive polymer electrode is positioned along the length of the distal end portion of the lead to deliver cardioverting and/or defibrillating electrical stimuli to the right ventricle of the heart.

55. The lead of claim 53 in which:

the conductive polymer electrode is positioned along the length of the distal end portion of the lead to deliver cardioverting and/or defibrillating electrical stimuli to the left ventricle of the heart.

56. The lead of claim 55 in which:

the conductive polymer electrode is positioned along the length of the distal end portion of the lead so as to contact a wall of a vessel in the coronary sinus region of the heart.

57. The lead of claim 49 in which:

the conductive polymer electrode and the tubular insulating housing are isodiametric.

58. The lead of claim 49 in which:

the second conductor is a coil conductor.

59. The lead of claim 58 in which:

the first and second conductors comprise coaxial coil conductors, the first conductor being disposed within the lumen of the second coil conductor.

60. The lead of claim 49 in which:

the second conductor comprises at least one cable conductor.

61. The lead of claim 60 in which:

the at least one cable conductor is insulated except along the exposed section.

62. The lead of claim 49 in which:

the housing comprises a multilumen housing, each of the first and the second conductors being contained within a separate lumen of the multilumen housing.

63. The lead of claim 62 in which:

the first conductor comprises a coil conductor; and the second conductor comprises at least one cable conductor.

64. The lead of claim 63 in which:

the second conductor comprises two cable conductors.

65. The lead of claim 49 in which:

each of the first and the second electrical conductors comprises a cable conductor.

66. The lead of claim 49 in which:

the conductive polymer electrode comprises a polymer formulated to be intrinsically conductive.

67. The lead of claim 66 in which:

the conductive polymer is selected from the group consisting of polyacetylene, polypyrrole, polyaniline, polythiophene, fluorophenyl thiophene, polyphenylene vinylene, polyphenylene sulfide, polynaphthalene, and polyphenylene.

68. The lead of claim 49 in which:

the conductive polymer electrode comprises an insulating, biocompatible polymer having conductive particles dispersed therein.

69. The lead of claim 68 in which:

the insulating polymer is selected from the group consisting of silicone rubber, polyurethane, and styrene-ethylene-butylene-styrene block polymer.

70. The lead of claim 68 in which:

the conductive particles comprise particles selected from the group consisting of silver, stainless steel, iridium, silver-coated nickel, carbon black, graphite, tantalum, palladium, titanium, platinum, gold, MP35N, fullerines, and carbon nanotubes.

71. The lead of claim 49 in which:

the conductive polymer electrode comprises a molded structure.

72. A body implantable lead adapted to transmit electrical signals between a proximal end of the lead and a distal end portion of the lead, the distal end portion of the lead including a tip electrode adapted to engage cardiac tissue and to electrically stimulate the tissue and/or sense electrical stimuli therefrom, the lead comprising:

a tip electrode conductor connecting the proximal end of the lead with the tip electrode;

at least one additional electrical conductor extending from the proximal end of the lead into the distal end portion of the lead;

a generally tubular insulating, multilumen housing of biocompatible, biostable material extending between the proximal end and the distal end portion of the lead, the tip electrode conductor being contained within a first lumen of the multilumen housing and the at least one additional electrical conductor being contained within at least one of the remaining lumens of the multilumen housing, the housing enclosing the at least one additional electrical conductor except along an exposed section thereof, the exposed section of the at least one additional conductor being disposed within the distal end portion of the lead; and a conductive polymer electrode contained within a window formed in the multilumen housing, the electrode encapsulating the exposed section of the at least one additional conductor and being in electrical contact with the exposed section, the conductive polymer being adapted to engage cardiac tissue and to perform one or more of the functions consisting of pacing, sensing, cardioversion and defibrillation, wherein the exposed section of the conductor encapsulated by the conductive polymer electrode includes area-increasing structure for enhancing the bond between the electrode and the conductor.

73. The lead of claim 72 in which:

the tip electrode conductor comprises a coil conductor.

74. The lead of claim 72 in which:

the at least one additional conductor comprises a cable conductor.

75. The lead of claim 74 in which:

the cable conductor comprises a multistrand conductor.

76. The lead of claim 74 in which:

the tip electrode conductor comprises a cable conductor.

77. The lead of claim 76 in which:

the tip electrode cable conductor comprises a multistrand conductor.

78. The lead of claim 72 in which:

the area-increasing structure is selected from the group consisting of a roughened surface of the cable conductor, a knurled surface of the cable conductor, projections extending from a surface of the cable conductor, beads attached to a surface of the cable conductor, mesh attached to a surface of the cable conductor, longitudinally spaced apart wire loops attached to a surface of the cable conductor, and wire wound around and attached to a surface of the cable conductor.

79. The lead of claim 72 in which:

the multilumen housing includes a lumen containing a polymer liner for guiding a stylet during implantation of the lead.

80. The lead of claim 79 in which:

the polymer lining is made of PTFE.

81. The lead of claim 72 in which:

the conductive polymer electrode and the tubular housing are isodiametric.

82. The lead of claim 72 in which:

the conductive polymer electrode is positioned along the length of the distal end portion of the lead assembly to deliver cardioverting and/or defibrillating electrical stimuli to the tissue of the superior vena cava.

83. The lead of claim 72 in which:

the conductive polymer electrode is positioned along the length of the distal end portion of the lead to deliver cardioverting and/or defibrillating electrical stimuli to the tissue of a ventricle of the heart.

84. The lead of claim 72 in which:

the conductive polymer electrode is positioned along the length of the distal end portion of the lead to deliver cardioverting and/or defibrillating electrical stimuli to the coronary sinus of the heart.

85. The lead of claim 72 in which:

the conductive polymer electrode is positioned along the length of the distal end portion of the lead to deliver cardioverting and/or defibrillating electrical stimuli to a vein overlying the left side of the heart.

86. The lead of claim 72 in which:

the distal end portion of the lead body has an outer circumferential surface, the window extending about a portion of the outer circumferential surface.

87. The lead of claim 72 in which:

the conductive polymer electrode comprises at least two electrode sections disposed within a corresponding number of windows formed in the lead body and spaced apart along the length thereof.

88. The lead of claim 72 in which:

the conductive polymer comprises a polymer formulated to be intrinsically conductive.

89. The lead of claim 88 in which:

the conductive polymer is selected from the group consisting of polyacetylene, polypyrrole, polyaniline, polythiophene, fluorophenyl thiophene, polyphenylene vinylene, polyphenylene sulfide, polynaphthalene, and polyphenylene.

90. The lead of claim 72 in which:

the conductive polymer comprises an insulating, biocompatible polymer having conductive particles dispersed therein.

91. The lead of claim 90 in which:

the insulating polymer is selected from the group consisting of silicone rubber, polyurethane, and styrene-ethylene-butylene-styrene block polymer.

92. The lead of claim 90 in which:

the conductive particles comprise particles selected from the group consisting of silver, stainless steel, iridium, silver-coated nickel, carbon black, graphite, tantalum, palladium, titanium, platinum, gold, MP35N, fullerines, and carbon nanotubes.

93. An implantable lead comprising:

a lead body having a proximal end portion and a distal end portion;

a first conductive polymer electrode disposed along the distal end portion of the lead body for performing one or more of the functions consisting of pacing, sensing, cardioversion and defibrillation;

a first cable conductor contained within the lead body and extending from the proximal end portion into the distal end portion of the lead body, the conductive polymer electrode encapsulating the cable conductor and being in electrical contact therewith along the length of the conductive polymer electrode;

a second conductive polymer electrode disposed along the distal end portion of the lead body for performing one or more of the functions of pacing, sensing, cardioversion and defibrillation, the second conductive polymer electrode being longitudinally spaced apart from the first conductive polymer electrode; and a second cable conductor contained within the lead body and extending from the proximal end portion into the distal end portion of the lead body, the second conductive polymer electrode encapsulating the second cable conductor and being in electrical contact therewith along the length of the second conductive polymer electrode, wherein the portion of the conductor encapsulated by the conductive polymer electrode includes area-increasing structure for enhancing the bond between the electrode and the cable conductor.

94. The lead of claim 93 in which:
the first and second conductive polymer electrodes are disposed within windows formed in the lead body.

95. The lead of claim 93 in which:
the distal end portion of the lead body is adapted for implantation within the right side of a heart;
the first mentioned conductive polymer electrode is positioned along the length of the distal end portion of the lead body to deliver cardioverting/defibrillating electrical stimuli to the tissue of the right ventricle of the heart; and
the second conductive polymer electrode is positioned along the length of the distal end portion of the lead body to deliver cardioverting/defibrillating electrical stimuli to the tissue of the superior vena cava of the heart.

96. The lead of claim 93 in which:
the distal end portion of the lead body is adapted for left side implantation;
the first mentioned conductive polymer electrode is positioned along the length of the distal end portion of the lead body to deliver cardioverting/defibrillating electrical stimuli to the wall of a vessel within the coronary sinus region of the heart; and
the second conductive polymer electrode is positioned along the length of the distal end portion of the lead body to deliver cardioverting/defibrillating electrical stimuli to the tissue of the superior vena cava of the heart.

97. The lead as of claim 96 in which:
the distal end portion of the lead body is isodiametric.

98. The lead of claim 93 in which:
the distal end portion of the lead body is adapted for left side implantation;
the first mentioned conductive polymer electrode is positioned along the length of the distal end portion of the lead body to deliver cardioverting/defibrillating electrical stimuli to the coronary sinus of the heart; and
the second conductive polymer electrode is positioned along the length of the distal end portion of the lead body to deliver cardioverting/defibrillating electrical stimuli to a vein overlying the left side of the heart.

99. The lead as of claim 98 in which:
the distal end portion of the lead body is isodiametric.

100. The lead of claim 93 in which:
the lead body includes a multilumen housing, a first one of the lumens of the housing containing the first mentioned cable conductor and a second one of the lumens containing the second cable conductor.

101. The lead of claim 100 in which:
the multilumen housing includes a third lumen, the third lumen containing a lining extending from the proximal end portion of the lead body to the distal end portion thereof, the lining passing through the lengths of the first and the second conductive polymer electrodes and being encapsulated thereby, the lining being adapted to guide a stylet during implantation of the lead.

102. The lead of claim 93 in which:
the area-increasing structure is selected from the group consisting of a roughened surface of the cable conductor, a knurled surface of the cable conductor, projections extending from a surface of the cable conductor, beads attached to a surface of the cable conductor, mesh attached to a surface of the cable conductor, longitudinally spaced apart wire loops attached to a surface of the cable conductor, and wire wound around and attached to a surface of the cable conductor.

103. The lead of claim 93 in which:
each conductive polymer electrode comprises a polymer formulated to be intrinsically conductive.

104. The lead of claim 103 in which:
the polymer is selected from the group consisting of polyacetylene, polypyrrole, polyaniline, polythiophene, fluorophenyl thiophene, polyphenylene vinylene, polyphenylene sulfide, polynaphthalene, and polyphenylene.

105. The lead of claim 93 in which:
each conductive polymer electrode comprises an insulating, biocompatible polymer having conductive particles dispersed therein.

106. The lead of claim 105 in which:
the insulating polymer is selected from the group consisting of silicone rubber, polyurethane, and styrene-ethylene-butylene-styrene block polymer.

107. The lead of claim 105 in which:
the conductive particles comprise particles selected from the group consisting of silver, stainless steel, iridium, silver-coated nickel, carbon black, graphite, tantalum, palladium, titanium, platinum, gold, MP35N, fullerines, and carbon nanotubes.

108. The lead of claim 93 in which:
each of the conductive polymer electrodes comprises a molded structure.

109. A body implantable lead suitable for electrically simulating and/or sensing the tissue of the left side of the heart, the lead comprising:
a lead body having an isodiametric distal end portion configured to passively anchor the lead in the coronary sinus region of the heart;
a distal tip electrode adapted to be placed in a vessel in the coronary sinus region;
at least one conductive polymer electrode disposed along the distal end portion of the lead proximally of the tip electrode, the conductive polymer electrode being positioned along the distal end portion of the lead body so as to be placed in a vessel in the coronary sinus region, the at least one conductive polymer electrode being adapted to perform one or more of the functions consisting of pacing, sensing, cardioversion and defibrillation;

a first electrical conductor within the lead body coupling the tip electrode with a connector assembly at the proximal end of the lead body; and a second electrical conductor within the lead body coupling the conductive polymer electrode with the connector assembly, wherein the portion of the conductor coupled to the conductive polymer electrode includes area-increasing structure for enhancing the bond between the electrode and the conductor.

110. The lead of claim 109 in which:

the at least one conductive polymer electrode comprises a ring sensing electrode for sensing electrical signals generated by the left side of the heart.

111. The lead of claim 107 in which:

the at least one conductive polymer electrode is disposed within a window formed in the lead body.

112. The lead of claim 111 in which:

the distal end portion of the lead body has an outer circumferential surface, the window extending about a portion of the outer circumferential surface.

113. The lead of claim 109 in which:

the at least one conductive polymer electrode comprises a cardioverting/defibrillating electrode positioned along the distal end portion of the lead body and configured to deliver electrical shocks to the coronary sinus region of the heart.

114. The lead of claim 109 in which includes:

a second conductive polymer electrode disposed along the distal end portion of the lead body, the second conductive polymer electrode being positioned along the distal end portion of the lead body and being configured to deliver electrical cardioverting/defibrillating shocks to the coronary sinus region of the heart; and a third electrical conductor within the lead body coupling the second conductive polymer electrode with the connector assembly.

115. The lead of claim 114 in which:

each of the conductive polymer electrodes is disposed in a window formed in the lead body.

116. The lead of claim 114 in which:

the lead body includes a multilumen housing, each of the first, second and third electrical conductors being contained in separate ones of the lumens of the multilumen housing.

117. The lead of claim 109 in which includes:

a second conductive polymer electrode disposed along the distal end portion of the lead body, the second conductive polymer electrode being positioned along the distal end portion of the lead body and being configured to deliver electrical cardioversion/defibrillating shocks to the superior vena cava of the heart; and a third electrical conductor within the lead body coupling the second conductive polymer electrode with the connector assembly.

118. The lead of claim 117 in which:

each of the conductive polymer electrodes is disposed in a window formed in the lead body.

119. The lead of claim 117 in which:

the lead body includes a multilumen housing, each of the first, second and third electrical conductors being contained in separate ones of the lumens of the multilumen housing.

120. The lead of claim 109 in which:

the second electrical conductor comprises a cable conductor.

121. The lead of claim 120 in which:

a portion of the cable conductor is encapsulated by the at least one conductive polymer electrode.

122. The lead of claim 121 in which:

the area-increasing structure is selected from the group consisting of a roughened surface of the cable conductor, a knurled surface of the cable conductor, projections extending from a surface of the cable conductor, beads attached to a surface of the cable conductor, mesh attached to a surface of the cable conductor, longitudinally spaced apart wire loops attached to a surface of the cable conductor, and wire wound around and attached to a surface of the cable conductor.

123. The lead of claim 109 in which:

the at least one conductive polymer electrode comprises a polymer formulated to be intrinsically conductive.

124. The lead of claim 123 in which:

the polymer is selected from the group consisting of polyacetylene, polypyrrole, polyaniline, polythiophene, fluorophenyl thiophene, polyphenylene vinylene, polyphenylene sulfide, polynaphthalene, and polyphenylene.

125. The lead of claim 109 in which:

the at least one conductive polymer electrode comprises an insulating, biocompatible polymer having conductive particles dispersed therein.

126. The lead of claim 125 in which:

the insulating polymer is selected from the group consisting of silicone rubber, polyurethane, and styrene-ethylene-butylene-styrene block polymer.

127. The lead of claim 125 in which:

the conductive particles comprise particles selected from the group consisting of silver, stainless steel, iridium, silver-coated nickel, carbon black, graphite, tantalum, palladium, titanium, platinum, gold, MP35N, fullerines, and carbon nanotubes.

128. The lead of claim 109 in which:

the at least one conductive polymer electrode comprises a molded structure.

* * * * *